US011744937B2

(12) United States Patent
Searle et al.

(10) Patent No.: US 11,744,937 B2
(45) Date of Patent: Sep. 5, 2023

(54) FLEXIBLE AND CONFORMAL PATCH PUMP

(71) Applicant: Becton, Dickinson and Company, Franklin Lakes, NJ (US)

(72) Inventors: Gary Searle, Norfolk, MA (US); Keith N. Knapp, Warwick, NY (US); Peter Skutnik, Midland Park, NJ (US); Aidan Petrie, Franklin Lakes, NJ (US); Dan Nelsen, Franklin Lakes, NJ (US); Paul Brown, Franklin Lakes, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 162 days.

(21) Appl. No.: 17/345,362

(22) Filed: Jun. 11, 2021

(65) Prior Publication Data

US 2021/0308367 A1 Oct. 7, 2021

Related U.S. Application Data

(60) Continuation of application No. 16/133,276, filed on Sep. 17, 2018, now Pat. No. 11,052,189, which is a
(Continued)

(51) Int. Cl.
*A61M 5/142* (2006.01)
*A61M 5/168* (2006.01)
(Continued)

(52) U.S. Cl.
CPC .... *A61M 5/14244* (2013.01); *A61M 5/16804* (2013.01); *A61B 5/14532* (2013.01);
(Continued)

(58) Field of Classification Search
CPC .. A61M 2005/1726; A61M 2205/3569; A61M 2205/82; A61M 2230/201; A61M 5/14248
(Continued)

(56) References Cited

U.S. PATENT DOCUMENTS 2,103,389 A 12/1937 Salfisberg
2,962,192 A 11/1960 Volckening
(Continued)

FOREIGN PATENT DOCUMENTS

AU 2007201159 A1 4/2007
EP 0980687 A2 2/2000
(Continued)

*Primary Examiner* — Phillip A Gray
(74) *Attorney, Agent, or Firm* — Dickinson Wright PLLC

(57) ABSTRACT

Provided is a flexible and conformal wearable, self-contained medical device. The medical device comprises an integral housing formed by a flexible upper portion and a flexible lower portion joined along their perimeters. The medical device is also provided in a plurality of shapes and configurations for increasing the flexibility and conformability of the housing. The components contained within the housing, such as a drug reservoir, printed circuit board, and power supply are preferably constructed from flexible materials and are formed, connected and positioned according to the configuration of the housing in a manner for enhancing flexibility of the housing. A thermal bubble micropump is provided for controlling flow of a drug from the flexible reservoir, that utilizes a thermal resistor provided locally to a thermal expansion fluid that causes a surrounding membrane to expand and displace a volume of drug to be provided to the user.

14 Claims, 21 Drawing Sheets

Related U.S. Application Data division of application No. 12/585,062, filed on Sep. 2, 2009, now Pat. No. 10,092,691.

(51) Int. Cl.
  *A61B 5/145* (2006.01)
  *A61M 5/172* (2006.01)
  *A61M 5/158* (2006.01)

(52) U.S. Cl.
  CPC ........ *A61B 5/14542* (2013.01); *A61M 5/1723* (2013.01); *A61M 2005/14252* (2013.01); *A61M 2005/1583* (2013.01); *A61M 2205/36* (2013.01); *Y10T 29/49826* (2015.01)

(58) Field of Classification Search
  USPC ............. 604/133, 27, 19, 28, 30, 48, 65, 67, 604/93.01, 95.01, 117, 156, 131, 256, 604/264, 500–506, 890.1, 132
  See application file for complete search history.

(56) References Cited

U.S. PATENT DOCUMENTS

| | | |
|---|---|---|
| 3,857,382 A | 12/1974 | Williams, Jr. et al. |
| 3,963,380 A | 6/1976 | Thomas, Jr. et al. |
| 4,204,538 A | 5/1980 | Cannon |
| 4,734,092 A | 3/1988 | Millerd |
| 4,755,173 A | 7/1988 | Konopka et al. |
| 4,723,947 A | 9/1988 | Konopka |
| 5,176,662 A | 1/1993 | Bartholomew et al. |
| 5,226,899 A | 7/1993 | Lee et al. |
| 5,257,980 A | 11/1993 | Van Antwerp et al. |
| 5,320,600 A * | 6/1994 | Lambert ............... A61B 17/205 600/556 |
| 5,453,099 A | 9/1995 | Lee et al. |
| 5,522,803 A | 6/1996 | Teissen-Simony |
| 5,536,249 A | 7/1996 | Castellano et al. |
| 5,545,143 A | 8/1996 | Fischell |
| 5,545,152 A | 8/1996 | Funderburk et al. |
| 5,575,770 A | 11/1996 | Melsky et al. |
| 5,593,390 A | 1/1997 | Castellano et al. |
| 5,728,074 A | 3/1998 | Castellano et al. |
| 5,820,602 A | 10/1998 | Kovelman et al. |
| 5,851,197 A | 12/1998 | Marano et al. |
| 5,858,001 A | 1/1999 | Tsais et al. |
| 5,858,005 A | 1/1999 | Kriesel |
| 5,925,021 A | 7/1999 | Castellano et al. |
| 5,957,895 A | 9/1999 | Sage et al. |
| 5,968,011 A | 10/1999 | Larsen et al. |
| 5,980,506 A | 11/1999 | Mathiasen |
| 6,017,328 A | 1/2000 | Fischell et al. |
| 6,056,718 A | 5/2000 | Funderburk et al. |
| 6,068,615 A | 5/2000 | Brown et al. |
| 6,074,369 A | 6/2000 | Sage et al. |
| 6,086,575 A | 7/2000 | Mejslov |
| 6,093,172 A | 7/2000 | Funderburk et al. |
| 6,110,148 A | 8/2000 | Brown et al. |
| 6,123,690 A | 9/2000 | Mejslov |
| 6,126,609 A | 10/2000 | Keith et al. |
| 6,175,752 B1 | 1/2001 | Say et al. |
| 6,254,586 B1 | 7/2001 | Mann et al. |
| 6,272,364 B1 | 8/2001 | Kurnik |
| 6,275,717 B1 | 8/2001 | Gross et al. |
| 6,277,627 B1 | 8/2001 | Hellinga |
| 6,293,925 B1 | 9/2001 | Safabash et al. |
| 6,302,866 B1 | 10/2001 | Marggi |
| 6,352,523 B1 | 3/2002 | Brown et al. |
| 6,355,021 B1 | 3/2002 | Nielsen et al. |
| 6,391,005 B1 | 5/2002 | Lum et al. |
| 6,485,461 B1 | 11/2002 | Mason et al. |
| 6,485,462 B1 | 11/2002 | Kriesel |
| 6,520,938 B1 | 2/2003 | Funderburk et al. |
| 6,521,446 B2 | 2/2003 | Hellinga |
| 6,544,212 B2 | 4/2003 | Galley et al. |
| 6,546,269 B1 | 4/2003 | Kurnik |
| 6,551,276 B1 | 4/2003 | Mann et al. |
| 6,558,351 B1 | 5/2003 | Steil et al. |
| 6,565,509 B1 | 5/2003 | Say et al. |
| 6,576,430 B1 | 6/2003 | Hsieh et al. |
| 6,579,267 B2 | 6/2003 | Lynch et al. |
| 6,589,229 B1 | 7/2003 | Connelly et al. |
| 6,607,509 B2 | 8/2003 | Bobroff et al. |
| 6,656,158 B2 | 12/2003 | Mahoney et al. |
| 6,656,159 B2 | 12/2003 | Flaherty |
| 6,669,669 B2 | 12/2003 | Flaherty et al. |
| 6,692,457 B2 | 2/2004 | Flaherty |
| 6,699,218 B2 | 3/2004 | Flaherty et al. |
| 6,706,159 B2 | 3/2004 | Moerman et al. |
| 6,723,072 B2 | 4/2004 | Flaherty et al. |
| 6,740,059 B2 | 5/2004 | Flaherty |
| 6,749,560 B1 | 6/2004 | Konstrorum et al. |
| 6,749,587 B2 | 6/2004 | Flaherty |
| 6,768,425 B2 | 7/2004 | Flaherty et al. |
| 6,830,558 B2 | 12/2004 | Flaherty et al. |
| 6,830,562 B2 | 12/2004 | Mogensen et al. |
| 6,840,922 B2 | 1/2005 | Nielsen et al. |
| 6,852,104 B2 | 2/2005 | Blomquist |
| 6,949,084 B2 | 9/2005 | Marggi et al. |
| 6,960,162 B2 | 11/2005 | Saadat et al. |
| 6,960,192 B1 | 11/2005 | Flaherty et al. |
| 6,977,180 B2 | 12/2005 | Hellinga et al. |
| 6,997,907 B2 | 2/2006 | Safabash et al. |
| 7,004,928 B2 | 2/2006 | Aceti et al. |
| 7,018,360 B2 | 3/2006 | Flaherty et al. |
| 7,029,455 B2 | 4/2006 | Flaherty |
| 7,052,251 B2 | 5/2006 | Nason et al. |
| 7,064,103 B2 | 6/2006 | Pitner et al. |
| 7,070,580 B2 | 7/2006 | Nielsen |
| 7,083,597 B2 | 8/2006 | Lynch et al. |
| 7,109,878 B2 | 9/2006 | Mann et al. |
| 7,128,727 B2 | 10/2006 | Flaherty et al. |
| 7,137,964 B2 | 11/2006 | Flaherty |
| 7,144,384 B2 | 12/2006 | Gorman et al. |
| 7,207,974 B2 | 4/2007 | Safabash et al. |
| 7,214,207 B2 | 5/2007 | Lynch et al. |
| 7,226,278 B2 | 6/2007 | Nason et al. |
| 7,303,543 B1 | 12/2007 | Maule et al. |
| 7,303,549 B2 | 12/2007 | Flaherty et al. |
| 7,310,544 B2 | 12/2007 | Brister et al. |
| 7,318,816 B2 | 1/2008 | Bobroff et al. |
| 7,329,239 B2 | 2/2008 | Safabash et al. |
| 7,354,420 B2 | 4/2008 | Steil et al. |
| 7,496,392 B2 | 2/2009 | Alarcon et al. |
| 2002/0022798 A1 | 2/2002 | Connelly et al. |
| 2002/0040208 A1 | 4/2002 | Flaherty et al. |
| 2002/0012374 A1 | 9/2002 | Rake et al. |
| 2003/0055380 A1 | 3/2003 | Flaherty |
| 2003/0109829 A1 | 6/2003 | Mogensen et al. |
| 2003/0176852 A1 | 9/2003 | Lynch et al. |
| 2003/0199823 A1 | 10/2003 | Bobroff et al. |
| 2003/0204161 A1 | 10/2003 | Ferek-Petric |
| 2004/0002682 A1 | 1/2004 | Kovelman et al. |
| 2004/0010207 A1 | 1/2004 | Flaherty et al. |
| 2004/0059316 A1 | 3/2004 | Smedegaard |
| 2004/0064096 A1 | 4/2004 | Flaherty et al. |
| 2004/0078028 A1 | 4/2004 | Flaherty et al. |
| 2004/0092865 A1 | 5/2004 | Flaherty et al. |
| 2004/0092878 A1 | 5/2004 | Flaherty |
| 2004/0116866 A1 | 6/2004 | Gorman et al. |
| 2004/0127844 A1 | 7/2004 | Flaherty |
| 2004/0153032 A1 | 8/2004 | Garribotto et al. |
| 2004/0204673 A1 | 10/2004 | Flaherty |
| 2004/0204687 A1 | 10/2004 | Mogensen et al. |
| 2004/0220551 A1 | 11/2004 | Flaherty et al. |
| 2004/0235446 A1 | 11/2004 | Flaherty et al. |
| 2004/0260233 A1 | 12/2004 | Garibotto et al. |
| 2005/0021005 A1 | 1/2005 | Flaherty et al. |
| 2005/0022274 A1 | 1/2005 | Campbell et al. |
| 2005/0043687 A1 | 2/2005 | Mogensen et al. |
| 2005/0065466 A1 | 3/2005 | Vedrine et al. |
| 2005/0065760 A1 | 3/2005 | Murtfeldt et al. |
| 2005/0075624 A1 | 4/2005 | Miesel |
| 2005/0090784 A1 | 4/2005 | Nielsen et al. |

(56) References Cited

U.S. PATENT DOCUMENTS

| | | |
|---|---|---|
| 2005/0101932 A1 | 5/2005 | Cote et al. |
| 2005/0101933 A1 | 5/2005 | Marrs et al. |
| 2005/0113761 A1 | 5/2005 | Faust et al. |
| 2005/0124936 A1 | 6/2005 | Mogensen et al. |
| 2005/0171512 A1 | 8/2005 | Flaherty |
| 2005/0182366 A1 | 8/2005 | Vogt et al. |
| 2005/0215982 A1 | 9/2005 | Malave et al. |
| 2005/0222645 A1 | 10/2005 | Malave et al. |
| 2005/0238507 A1 | 10/2005 | Dilanni et al. |
| 2005/0245799 A1 | 11/2005 | Brauker et al. |
| 2005/0245839 A1 | 11/2005 | Stivoric et al. |
| 2005/0273076 A1 | 12/2005 | Beasley et al. |
| 2005/0283144 A1 | 12/2005 | Shiono et al. |
| 2006/0030838 A1 | 2/2006 | Gonnelli |
| 2006/0041229 A1 | 2/2006 | Garibotto et al. |
| 2006/0074381 A1 | 4/2006 | Malave et al. |
| 2006/0106345 A1 | 5/2006 | Flaker et al. |
| 2006/0129090 A1 | 6/2006 | Moberg et al. |
| 2006/0135913 A1 | 6/2006 | Ethelfeld |
| 2006/0142698 A1 | 6/2006 | Ethelfeld |
| 2006/0178633 A1 | 8/2006 | Garibotto et al. |
| 2006/0200073 A1 | 9/2006 | Radmer et al. |
| 2006/0241365 A1 | 10/2006 | Botvinick et al. |
| 2006/0263839 A1 | 11/2006 | Ward et al. |
| 2006/0264835 A1 | 11/2006 | Nielsen et al. |
| 2006/0281435 A1 | 12/2006 | Shearer et al. |
| 2006/0282290 A1 | 12/2006 | Flaherty et al. |
| 2007/0016149 A1 | 1/2007 | Hunn et al. |
| 2007/0021733 A1 | 1/2007 | Hansen et al. |
| 2007/0049865 A1 | 3/2007 | Radmer et al. |
| 2007/0073229 A1 | 3/2007 | Gorman et al. |
| 2007/0073559 A1 | 3/2007 | Stangel |
| 2007/0118405 A1 | 5/2007 | Campbell et al. |
| 2007/0191702 A1 | 8/2007 | Yodfat et al. |
| 2007/0191736 A1 | 8/2007 | Alden |
| 2007/0219496 A1 | 9/2007 | Kamen et al. |
| 2008/0051697 A1 | 2/2008 | Mounce et al. |
| 2008/0051698 A1 | 2/2008 | Mounce et al. |
| 2008/0051709 A1 | 2/2008 | Mounce et al. |
| 2008/0051710 A1 | 2/2008 | Moberg et al. |
| 2008/0051711 A1 | 2/2008 | Mounce et al. |
| 2008/0051714 A1 | 2/2008 | Moberg et al. |
| 2008/0051716 A1 | 2/2008 | Stutz |
| 2008/0051718 A1 | 2/2008 | Kavazov et al. |
| 2008/0051727 A1 | 2/2008 | Moberg et al. |
| 2008/0051730 A1 | 2/2008 | Bikovsky |
| 2008/0051738 A1 | 2/2008 | Griffin |
| 2008/0051765 A1 | 2/2008 | Mounce |
| 2008/0097321 A1 | 4/2008 | Mounce et al. |
| 2008/0097326 A1 | 4/2008 | Moberg et al. |
| 2008/0097327 A1 | 4/2008 | Bente et al. |
| 2008/0097328 A1 | 4/2008 | Moberg et al. |
| 2008/0097375 A1 | 4/2008 | Bikovsky |
| 2008/0097381 A1 | 4/2008 | Moberg et al. |
| 2008/0116647 A1 | 5/2008 | Anderson et al. |
| 2008/0119707 A1* | 5/2008 | Stafford ............... A61B 5/6833 604/27 |
| 2008/0132842 A1 | 6/2008 | Flaherty |
| 2008/0140048 A1 | 6/2008 | Keimel et al. |
| 2008/0147041 A1 | 6/2008 | Kristensen |
| 2008/0160492 A1 | 7/2008 | Campbell et al. |
| 2008/0194924 A1 | 8/2008 | Valk et al. |
| 2008/0215006 A1 | 9/2008 | Thorkild |
| 2008/0261255 A1 | 10/2008 | Tolosa et al. |
| 2008/0264261 A1 | 10/2008 | Kavazov et al. |
| 2008/0269680 A1 | 10/2008 | Ibranyan et al. |
| 2008/0269713 A1 | 10/2008 | Kavazov |
| 2008/0294028 A1 | 11/2008 | Brown |
| 2008/0306434 A1 | 12/2008 | Dobbies et al. |
| 2008/0312608 A1 | 12/2008 | Christoffersen et al. |
| 2009/0005724 A1 | 1/2009 | Regittnig et al. |
| 2009/0005728 A1 | 1/2009 | Weinert et al. |
| 2009/0012472 A1 | 1/2009 | Ahm et al. |
| 2009/0028824 A1 | 1/2009 | Chiang et al. |
| 2009/0043288 A1 | 2/2009 | Petrakis |
| 2009/0076453 A1 | 3/2009 | Mejlhede et al. |
| 2009/0112188 A1 | 4/2009 | Santini et al. |
| 2009/0198215 A1 | 8/2009 | Chong et al. |
| 2009/0204077 A1 | 8/2009 | Hasted et al. |
| 2009/0221971 A1 | 9/2009 | Mejlhede et al. |

FOREIGN PATENT DOCUMENTS

| | | |
|---|---|---|
| EP | 1447072 A1 | 8/2004 |
| EP | 1044374 B1 | 10/2008 |
| JP | H09500291 A | 1/1997 |
| JP | 2001513409 A | 9/2001 |
| JP | 2003243458 A | 8/2003 |
| JP | 2005526560 | 9/2005 |
| JP | 2006500508 A | 1/2006 |
| JP | 2007502169 A | 2/2007 |
| JP | 2009142661 A | 7/2009 |
| JP | 2009525822 | 7/2009 |
| JP | 2010507457 A | 3/2010 |
| WO | WO-9015638 A1 | 12/1990 |
| WO | WO-99011309 A1 | 3/1999 |
| WO | WO-2007051139 | 5/2007 |
| WO | WO-2007071255 A1 | 6/2007 |
| WO | WO-2008114218 A2 | 9/2008 |
| WO | WO-2009004026 A1 | 1/2009 |
| WO | WO-2009021039 | 2/2009 |
| WO | WO-2009021052 | 2/2009 |
| WO | WO-2009033032 A1 | 3/2009 |

* cited by examiner

FLEXIBLE AND CONFORMAL PATCH PUMP

CROSS-REFERENCE TO RELATED APPLICATIONS

This application is a continuation of U.S. patent application Ser. No. 16/133,276, filed Sep. 17, 2018, which is a divisional of U.S. patent application Ser. No. 12/585,062, filed Sep. 2, 2009 (now U.S. Pat. No. 10,092,691, issued Oct. 9, 2018), which is incorporated herein in its entirety.

FIELD OF THE INVENTION

The present invention relates generally to wearable, self-contained drug infusion devices provided in a discreet flexible and conformal housing for providing greater comfort, convenience, ease of use, and attractiveness for the user.

BACKGROUND OF THE INVENTION

Diabetes is a group of diseases marked by high levels of blood glucose resulting from defects in insulin production, insulin action, or both. There are 23.6 million people in the United States, or 8% of the population, who have diabetes. The total prevalence of diabetes has increased 13.5% since the 2005-2007 time period. Diabetes can lead to serious complications and premature death, but there are well-known products available for people with diabetes to help control the disease and lower the risk of complications.

Treatment options for people with diabetes include specialized diets, oral medications and/or insulin therapy. The primary goal for diabetes treatment is to control the patient's blood glucose (sugar) level in order to increase the chances of a complication-free life. It is not always easy, however, to achieve good diabetes management, while balancing other life demands and circumstances.

Currently, there are two principal modes of daily insulin therapy for the treatment of type 1 diabetes. The first mode includes syringes and insulin pens that require a needle stick at each injection, typically three to four times per day, but are simple to use and relatively low in cost. Another widely adopted and effective method of treatment for managing diabetes is the use of an insulin pump. Insulin pumps can help the user keep their blood glucose levels within target ranges based on their individual needs, by continuous infusion of insulin. By using an insulin pump, the user can match their insulin therapy to their lifestyle, rather than matching their lifestyle to how an insulin injection is working for them.

Conventional insulin pumps are capable of delivering rapid or short-acting insulin 24 hours a day through a catheter placed under the skin. Insulin doses are typically administered at a basal rate and in a bolus dose. Basal insulin is delivered continuously over 24 hours, and strives to keep one's blood glucose levels in a consistent range between meals and overnight. Some insulin pumps are capable of programming the basal rate of insulin to vary according to the different times of the day and night. Bolus doses are typically administered when the user takes a meal, and generally provide a single additional insulin injection to balance the carbohydrates consumed. Some conventional insulin pumps enable the user to program the volume of the bolus dose in accordance with the size or type of the meal consumed. Conventional insulin pumps also enable a user to take in a correctional or supplemental bolus of insulin to compensate for a low blood glucose level at the time the user is calculating a meal bolus.

There are many advantages of conventional insulin pumps over other methods of diabetes treatment. Insulin pumps deliver insulin over time rather than in single injections and thus typically result in less variation within the blood glucose range that is recommended by the American Diabetes Association. Conventional insulin pumps reduce the number of needle sticks which the patient must endure, and make diabetes management easier and more effective for the user, thus considerably enhancing the quality of the user's life. Insulin pumps however can be heavy and cumbersome to use and are typically more expensive than other methods of treatment. From a lifestyle standpoint, the conventional pump, tubing, and infusion set are inconvenient and bothersome for the user.

New advances in insulin therapy provide "wearable" drug infusion devices, such as patch pumps, that are lower in cost and are somewhat more convenient and comfortable to use than conventional insulin pumps. Some of these devices are intended to be partially or entirely disposable, and in theory provide many of the advantages of conventional insulin pumps without the initial high cost and inconvenience of conventional insulin pumps. Commonly available patch pumps, however, still do not provide the user with the utmost comfort and convenience to lend themselves to more widespread use. Typical patch pumps are still relatively heavy and bulky and are commonly constructed with a rigid housing containing rigid components, thus causing the user discomfort over a prolonged period of use. Such patch pumps tend to be especially uncomfortable for children, small women and the elderly, for whom the relatively large patch pumps are not ideal. Additionally, the construction of common patch pumps prevents the patch pump from being easily concealed and limits the number of locations on a user's body where it may be worn.

Accordingly, there is a need for more discreet drug infusion devices with improved convenience, comfort, and wearability, so that many more users may benefit from the advantages these devices provide.

SUMMARY OF THE INVENTION

Exemplary embodiments of the present invention address at least the above problems and/or disadvantages and provide at least the advantages described below. Accordingly, it is an object of certain embodiments of the present invention to provide more discreet, flexible and conformal, wearable drug infusion devices for increasing a user's convenience and comfort in using such devices.

According to one aspect of the present invention, a wearable medical device provided for administering drug therapy to a user comprises an integral housing containing a flexible reservoir for housing a supply of a drug, in fluid communication with an infusion cannula for delivering the drug to the user, and a fluid metering device for metering delivery of the drug from the reservoir to the user through the infusion cannula, wherein said housing comprises a flexible upper portion and a flexible lower portion that are sonically welded together along their respective perimeters. The upper and lower portions of the housing are constructed from a flexible polymer wherein the thickness of the integral housing is within a range of 0.25 to 1.25 inches, preferably no more than about 0.75 inches, and is affixed to the user's skin with an adhesive layer. A foam or elastomer layer may also be provided sandwiched between the adhesive layer and the lower portion of the medical device. The fluid metering device comprises at least one thermal resistor provided locally to a thermal expansion fluid encapsulated by a flexible membrane, wherein heating of said thermal expansion fluid causes expansion of said flexible membrane resulting in displacement of the drug and actuation of said drug into said user through the infusion needle. In one embodiment, a plurality of thermal resistors with expansion fluid and flexible membrane may be provided sequentially to create a linear peristaltic type flow of said drug to the user. The fluid metering device further comprises at least one one-way check valve for promoting a flow of the drug to said user. The fluid metering device may also comprise an electronically controlled gate or valve for controlling the flow of drug to said user. In one embodiment, the fluid metering device alternatively comprises one of a Belleville spring washer, stamped leaf spring, snap disk or flexure, for expelling the drug from said reservoir. The medical device further contains a flexible circuit board, provided with at least one recess extending inwardly from an outer edge of said circuit board, for electronically connecting at least the fluid metering mechanism with a controller.

According to this aspect of the present invention, the medical device is provided comprising a chassis, the chassis comprising at least a first frame flexibly connected to a second frame for positioning a first system component in said first frame and a second system component in said second frame relative to each other in said housing. The medical device further comprises an infusion needle deployment mechanism actuated by a push button deployable within said housing, wherein in one embodiment, said needle deployment mechanism comprises a spring disk for driving said infusion needle into the user. In another embodiment, the needle deployment mechanism comprises a torsion spring actuated by a finger lever for driving said infusion needle into the user. In yet another embodiment, the needle deployment mechanism comprises a needle carriage and a cannula carriage initially engaged with each other for driving a flexible cannula into the user using an insertion needle, and a spring member for withdrawing said insertion needle from the user upon insertion of said flexible cannula into the user. A similar needle carriage and biosensor carriage is also provided for inserting a biosensor into the user with the aid of an insertion needle, whereupon the needle is withdrawn from the user after insertion of the biosensor. The medical device also comprises a mechanism for manually actuating a bolus dose by applying a force to a specific area on said upper portion of said housing and a mechanism for deploying a transcutaneous analyte sensor for the purpose of determining the blood glucose level of the user, or some other physiological indicator.

Still according to this aspect of the invention, a second flexible reservoir is provided for housing a volume of drug for bolus dose delivery to the user. The second reservoir may be provided in fluid communication with a second infusion cannula and is preferably used for administering drug therapy to a user with type 2 diabetes. Additionally, the medical device in this embodiment provides a basal rate of drug infusion to the user and may be used in conjunction with a programmable injection device, such as an insulin pen, for providing bolus dose drug therapy. The programmable injection device is preferably programmed by a host device which also calculates the bolus dose of drug for injection into the user.

A second aspect of the present invention provides a wearable medical device for administering drug therapy to a user, comprising an integral housing comprising a flexible upper portion and a flexible lower portion, wherein said housing is formed into an elongate shape comprising a length dimension that is longer than a width dimension, and further comprising a waist portion that is narrower than the width dimension, said housing being contoured such that the housing is narrowest at the waist portion. The flexible upper and lower portions of the medical device are sonically welded together along their respective perimeters.

A third aspect of the present invention provides a wearable medical device for administering drug therapy to a user, comprising an integral housing comprised of a flexible upper portion and a flexible lower portion, wherein said upper and lower portions comprise at least one recess extending inwardly from an outer edge of each of said upper and lower portions. The medical device further comprises a second recess extending inwardly from an outer edge of each of said upper and lower portions at a location opposite the at least one recess. The first and second recesses of the upper and lower portions define a flex region that separates a first area of the device from a second area of the device. A first system component is contained within the first area and a second system component is contained within the second area.

Yet another aspect of the present invention provides a wearable medical device for administering drug therapy to a user, comprising an integral housing comprised of a flexible upper portion and a flexible lower portion, wherein said housing comprises a central hub area with a plurality of lobes extending radially from said central hub. A first system component of the medical device is contained within a first lobe, and a second system component is contained within a second lobe. The first system component and the second system component include one of a reservoir for delivering a bolus dose of a drug, a biosensor, a needle deployment mechanism, and a communication transceiver. The medical device further comprises at least one adhesive pad attached to a skin attachment side of said plurality of lobes.

A final aspect of the present invention provides a method for providing a flexible, wearable medical device for administering drug therapy to a user, by preparing a housing comprising an upper flexible portion and a lower flexible portion, providing within said housing, an infusion cannula in fluid communication with a reservoir for housing a drug to be administered to the user and a fluid metering mechanism that meters a volume of the drug administered through the infusion cannula, and forming the housing by connecting the upper flexible portion to the lower flexible portion along a perimeter of each. The method sonically welds the upper flexible portion to the lower flexible portion.

Objects, advantages and salient features of the invention will become apparent to those skilled in the art from the following detailed description, which, taken in conjunction with annexed drawings, discloses exemplary embodiments of the invention.

BRIEF DESCRIPTION OF THE DRAWINGS

The above and other exemplary features and advantages of certain exemplary embodiments of the present invention will become more apparent from the following description of certain exemplary embodiments thereof when taken in conjunction with the accompanying drawings, in which.

Throughout the drawings, like reference numerals will be understood to refer to like elements, features and structures.

DETAILED DESCRIPTION OF EXEMPLARY EMBODIMENTS

The matters exemplified in this description are provided to assist in a comprehensive understanding of exemplary embodiments of the invention, and are made with reference to the accompanying figures. Accordingly, those of ordinary skill in the art will recognize that various changes and modifications of the exemplary embodiments described herein can be made without departing from the scope and spirit of the claimed invention. Also, descriptions of well-known functions and constructions are omitted for clarity and conciseness.

Figure 1:
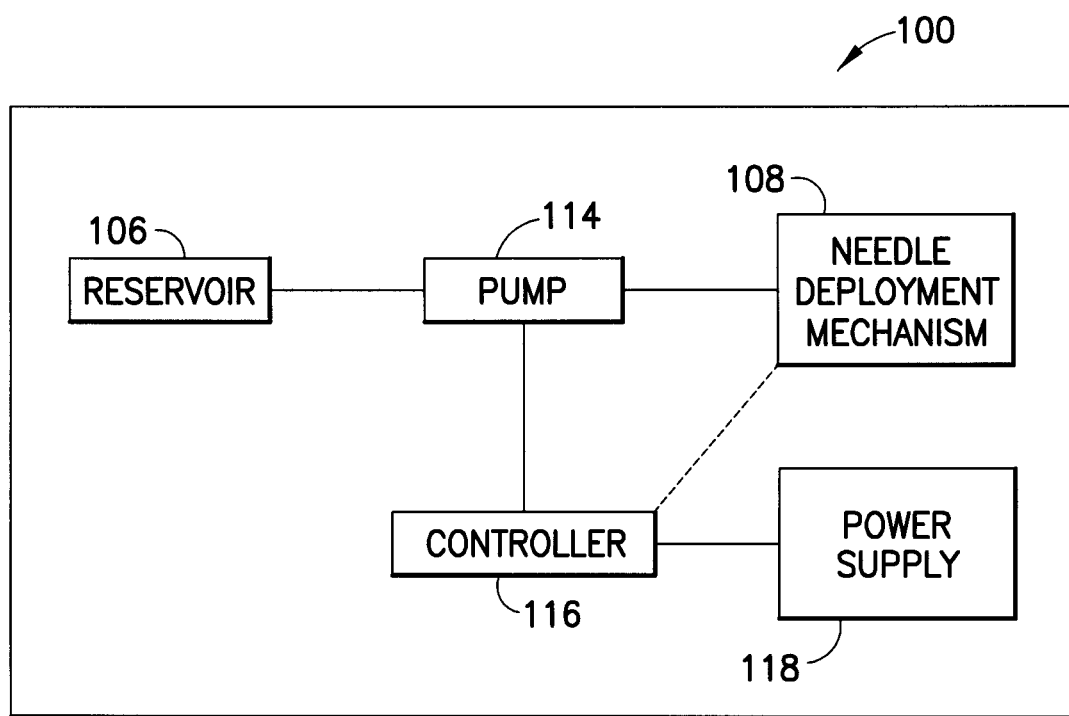
FIG. 1 is a block diagram illustrating the principal components of a medical device in accordance with an exemplary embodiment of the present invention.

A general embodiment of medical device 100 is illustrated in FIG. 1. Medical device 100 is preferably a wearable medical device provided for the delivery of a liquid or gel medication, preferably but not necessarily insulin, or other therapeutic substance, by continuous infusion into or through the skin of the patient. Medical device 100 is capable of providing subcutaneous, intradermal, intramuscular and intravenous infusion of the drug or substance. Such known medical devices are commonly referred to as "patch pumps" due to their nature of being worn or affixed to the user's skin. Medical device 100 generally comprises a housing for a flexible drug reservoir 106 or other container for supplying a drug, an infusion needle deployment mechanism 108 and a pump mechanism 114 or fluid metering device for controlling the delivery of the drug into the user's body through an infusion needle provided in the infusion needle deployment mechanism 108. Medical device 100 also preferably comprises a microprocessor or controller 116 for directing the infusion needle deployment mechanism 108 and pump mechanism 114 as well as monitoring and/or controlling other preferred operations and systems of medical device 100, and a power supply 118 such as any known power source including, but not limited to, a disposable or rechargeable standard battery, capacitor, or energy harvesting system such as that disclosed in commonly assigned and co-pending U.S. patent application Ser. No. 12/458,807, filed Jul. 23, 2009, which is incorporated herein by reference in its entirety.

One exemplary embodiment of medical device 100 is a pre-programmed patch pump. The pre-programmed patch pump can be programmed either by the manufacturing facility or a health care provider and preferably requires no additional user programming. A pre-programmed patch pump is ideal for certain patient groups, such as recently diagnosed type 1 diabetics, more specifically those that are elderly or mentally challenged and may have difficulty in programming the patch pump. Pre-programmed patch pumps may comprise simple intelligence for providing a customized basal infusion rate that can be varied throughout the day to match sleeping and waking insulin requirements. The preprogrammed patch pump can be programmed to deliver drug to the user at different rates for different times of day or under different conditions. Varying drug delivery rates over time are referred to herein as a drug delivery profile. The pre-programmed patch pump may also be designed with mechanization to enable manual actuation of an incremental bolus dose, for example 10 units. One form of manual actuation would require the closure of an electrical contact, such as a momentary switch or two momentary switches, for an extended duration. A separate second reservoir may be provided for supplying the bolus dose, and could utilize either the same cannula used for basal infusion or a second cannula. A pre-programmed patch pump may also be configured to provide multiple daily injections.

Medical device 100, in other embodiments of the present invention, may also be provided as a fully-programmable ("smart"), or substantially mechanical ("simple") package, as would be appreciated by one of ordinary skill in the art.

A fully-programmable "smart" patch pump provides the user with the greatest precision and flexibility in controlling the rate of administering a drug that is suitable for the user's lifestyle, but adds additional cost and complexity to the device. "Smart" patch pumps are generally used in conjunction with a Blood Glucose Monitor (BGM) and a host device, such as a Personal Diabetes Monitor (PDM), to provide, through closed-loop control and sensing, a customized basal infusion rate and bolus doses that may be activated or adjusted at any time throughout the day. "Smart" patch pumps are preferably configured to be in communication with the host device, such as via a personal area network as described in previously incorporated, co-pending U.S. patent application Ser. No. 12/458,807, or via a wireless network. "Smart" patch pumps may also communicate, continuously or intermittently, with the host device via a wired or other direct connection.

"Simple" patch pumps can be provided with minimal or no system intelligence and generally comprise mostly mechanical systems for providing basic control of insulin infusion through either a preset basal rate or manually activated bolus doses. The cost of "simple" patch pumps is greatly reduced compared to "smart" patch pumps, since the relatively expensive electronics necessary for realizing the specialized sensing, control and communication capabilities are not required.

Each patch pump package, "smart", pre-programmable, and "simple", is particularly effective and desired for a certain type of user or group of users. A user's lifestyle, medical condition, financial situation and aptitude for operating a medical device largely determine which package of patch pump is suitable for that user. The specific features and functionality of exemplary embodiments of the present invention, to follow, may be implemented in each of the patch pump packages described above. Additional embodiments, features and specific functionality of patch pumps to be used in accordance with the present invention can be found in U.S. Pat. No. 6,960,192 and U.S. Patent Application Publication No. 2004/0010207, both assigned to Insulet Corporation, commonly assigned U.S. Pat. No. 6,589,229 issued to Robert I Connelly, et al., and commonly assigned co-pending U.S. Patent Application titled "Extended Use Medical Device," filed on even date herewith, which are all incorporated herein by reference.

Exemplary embodiments of medical device 100 in accordance with the present invention are illustrated in FIGS. 2-5. Each of the exemplary embodiments depicted therein comprise a flexible upper and lower cover, shown as 202 and 204 in FIGS. 2, 302 and 304 in FIGS. 3A and 3C, 402 and 404 in FIG. 4, and 502 and 504 in FIG. 5A. In the exemplary embodiments of the present invention, the upper and lower covers make up an external shell or housing for medical device 100. Each of the upper and lower covers is preferably constructed from thin flexible polymers, such as polyethylene (PE), polypropylene (PP), or polyvinyl chloride (PVC). These materials are exemplary and are not intended to be limiting, and one of ordinary skill in the art will recognize that any suitable material for providing a thin flexible housing for the components of medical device 100 may be used. The upper and lower covers are preferably substantially similar in shape, so as to have matching or near matching perimeters. In an exemplary embodiment, the upper and lower covers are sonically welded together along the perimeter of each to securely encapsulate the components of medical device 100. The lower cover is preferably affixed to the user's skin via any well known, long-lasting adhesive layer 210 that is safe for skin contact with the user. As the lower cover of medical device 100 is affixed to the user, the lower cover conforms to the user and advantageously permits flexure of the entire medical device 100. The upper cover is preferably designed to minimize imparting resistance to the flexure and conformity of medical device 100. A housing for medical device 100 constructed in this manner is very thin, flexible and conformal to each user's unique body shapes. The minimal thickness and optimal flexibility of medical device 100 affords the user a level of convenience, versatility and comfort, not provided by conventional patch pumps.

It is also preferred, in exemplary embodiments of the present invention, that the chosen shape of the upper and lower covers be visibly attractive to the user and the public so as to enhance the overall perception of an exemplary medical device 100. To conceal the functionality of medical device 100, the upper cover may be designed to resemble a common bandage, or may be colored to blend with a user's skin tone. Additionally, the upper cover of each embodiment may be decorated with a custom design, artwork, or logo, to further enhance a visual appeal of the device for the user and signify a user's individuality, especially when worn by a child.

Figure 2:
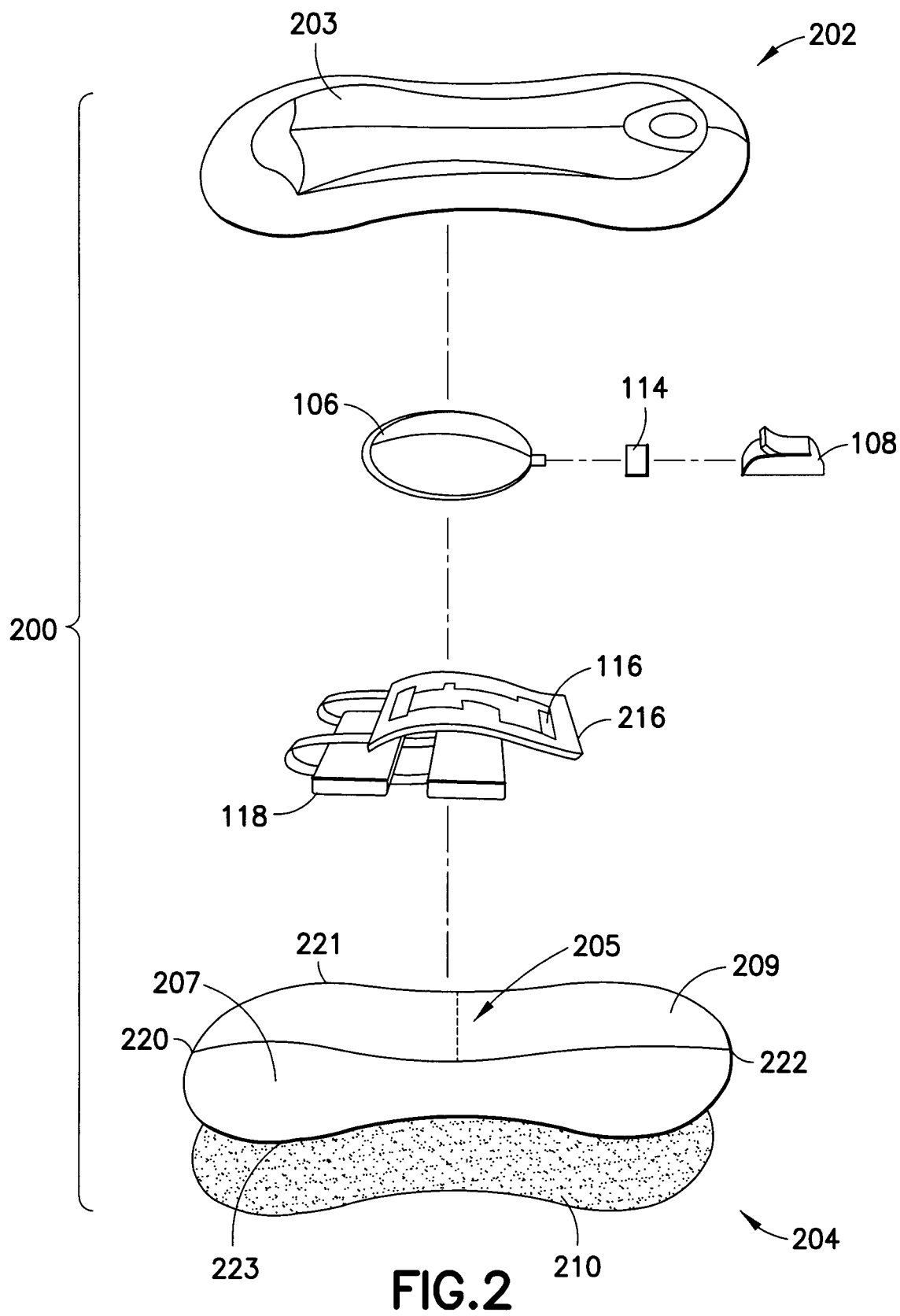
FIG. 2 is an illustration of a first exemplary embodiment of a medical device in accordance with an exemplary embodiment of the present invention.

The upper cover, in exemplary embodiments of the present invention, may be constructed to be slightly hardened, thicker, or more durable than the lower cover, in order to provide added protection for the internal components. To ensure optimal flexibility of medical device 100, it is not necessary that the entire surface of the upper cover be constructed in this manner. For instance, as shown in FIG. 2, part of the upper cover 202 with a smaller surface area 203 in a similar shape as the upper cover, may be constructed in the above manner to provide the added protection. In another embodiment, select areas of the upper cover may be constructed in this manner to provide added protection only to specific portions or components of medical device 100.

FIGS. 2 and 3 illustrate first and second exemplary embodiments of medical device 100 that provide two-dimensional conformity and flexibility in accordance with the present invention. The embodiment depicted in FIG. 2 is an elongate flexible medical device 200 that realizes a minimal thickness, but also provides increased surface area for skin adhesion to a user. The design of flexible upper cover 202 and flexible lower cover 204 provide increased conformity to cylindrical shapes, such as a user's arm. Flexibility and conformity of medical device 200 shown in FIG. 2 is increased by providing a "waist" 205 or reduced dimension of the mid-section of the elongate upper and lower covers. The medical device 200 has a length dimension defined as the longest dimension extending from a first edge 220 of the cover to a second opposite edge 222 of the cover. The medical device 200 has a width dimension defined as a longest dimension that is perpendicular to the primary dimension and spans from a third edge 221 to a fourth edge 223 of the cover opposite the third edge. The width of the device 200 is preferably contoured to be narrower at a midsection or "waist" 205. In the embodiment shown, the waist dissects the device 200 forming a first section 207 and a second section 209 opposite the first section, that are preferably symmetrical about the waist, such that the first and second section are of a similar shape and dimension.

The overall shape of upper cover 202 and lower cover 204 for medical device 200 in an exemplary embodiment illustrated in FIG. 2, is not specifically limited to the shape depicted. Alternate shapes and relative dimensions of upper cover 202 and lower cover 204, suitable for use in this embodiment, will be understood by one of ordinary skill in the art. For instance, in another embodiment, instead of providing the "waist" 205 or reduced section midway along the length dimension of the upper and lower covers, as shown in FIG. 2, the flexible upper and lower covers may comprise at least one waist section at any point along the length dimension. This waist section preferably comprises a dimension that is perpendicular to the length dimension and less than the width dimension. In this embodiment, it is not necessary that the upper and lower covers comprise a first and second section symmetrical about the at least one waist section, or that the waist section even dissects a first section and a second section equally. One of ordinary skill in the art will understand that any shape of a flexible upper and lower cover, 202 and 204, that is defined by the description provided above may be suitable for medical device 100 in the first exemplary embodiment.

Exemplary embodiments of the present invention, as illustrated in FIGS. 2-5, provide not only a flexible housing for medical device 100, as discussed above, but also preferably utilize flexible and low profile components within the housing to be specifically described further below, such as a flexible reservoir 106, flexible circuit board 216, flexible power supply 118, flexible electrical conductors between components, and low profile pump mechanism 114 and infusion needle deployment mechanism 108. The profile of medical device 100 may range in thickness from 0.25 inches to 1.25 inches, but is preferably no greater than 0.75 inches, depending on the specific functionality of medical device, that is, whether it is "smart", pre-programmed, or "simple", as well as the specific components chosen for needle deployment mechanism 108 and fluid metering mechanism 114, and the arrangement of such components. The specific components illustrated in FIG. 2 are not limited to this exemplary embodiment of the present invention and one of ordinary skill in the art will recognize that any combination and arrangement of components may be utilized in each of the exemplary embodiments illustrated and described with respect to FIGS. 2-5.

Figure 3A:
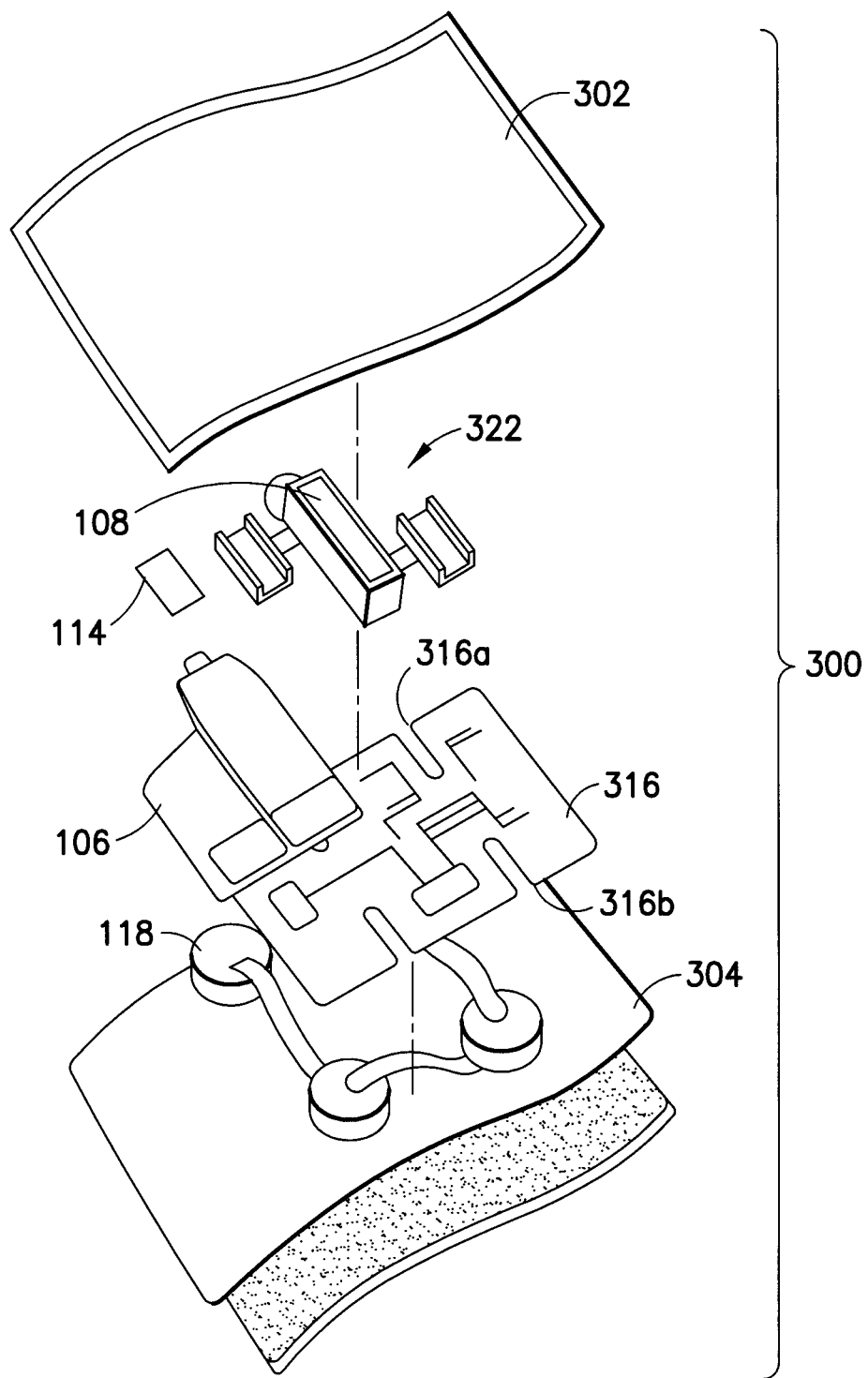
FIGS. 3A-3C illustrate a second exemplary embodiment of a medical device in accordance with an exemplary embodiment of the present invention.
Figure 3B:
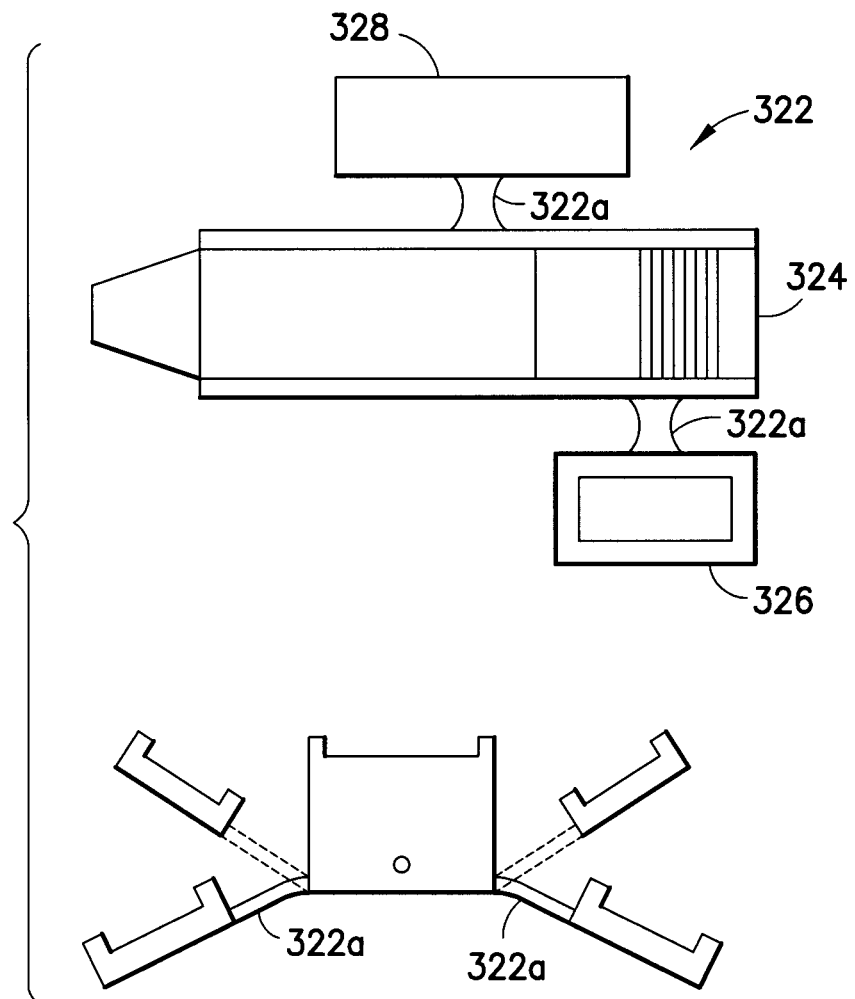
Figure 3C:
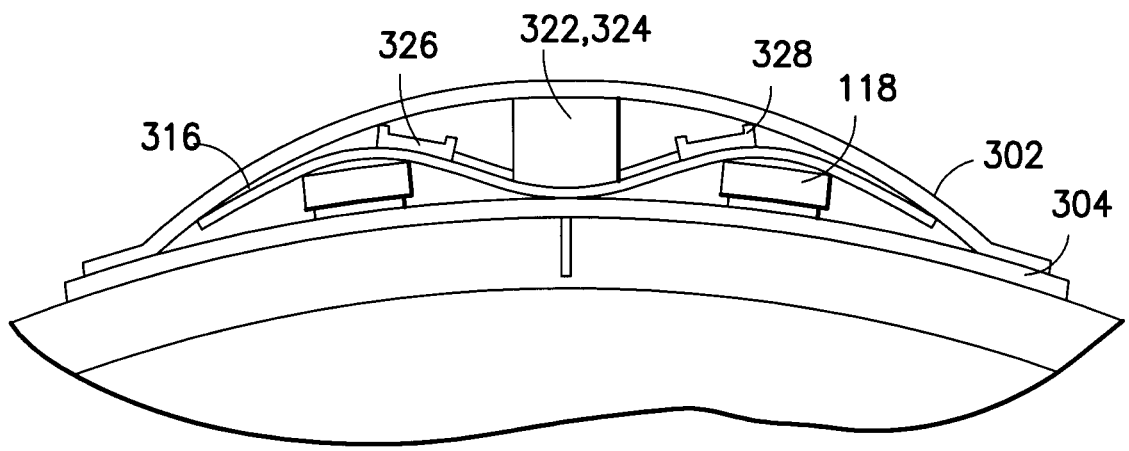

The flexible and conformal medical device 300 illustrated in FIGS. 3A-3C, is formed into a substantially rectangular package that resembles a familiar bandage, with a reduced surface area of coverage but increased thickness relative to the embodiment illustrated in FIG. 2. Flexible upper cover 302 and flexible lower cover 304 preferably provide optimal flexibility and conformity, as discussed above. Since the overall surface area or footprint of the flexible upper cover 302 and flexible lower cover 304 in this embodiment are reduced, it is not necessary to provide a reduced "waist" or midsection for aiding in conformity or flexibility. However, due to the reduced surface area of medical device 300, several of the desired components may be stacked or arranged on top of each other, as shown in FIG. 3C, resulting in the increased thickness of medical device 300. To maintain overall flexibility and conformity of medical device 300, it is necessary that the arrangement of the components do not inhibit the desired flexure of medical device 300, as will be described in further detail below.

The exemplary embodiment illustrated in FIG. 3A provides an exemplary flexible printed circuit board (PCB) 316 and a flexible chassis 322 for providing a flexible arrangement of the specific system components, ideal for use in medical device 100 with a reduced surface area as described above. The exemplary embodiment of a flexible printed circuit board 316 for use in this and other exemplary embodiments is shown in FIG. 3A. Flexible PCB 316 is modified in this embodiment to include slots, recesses or cutouts, 316a and 316b along the outer perimeter of PCB 316, as shown. This modification provides an additional degree of flexibility for the PCB 316 at locations that are preferably located between rigid system components, so as to enable the PCB to flex as necessary based on the close positioning of the other system components, as shown in FIG. 3C. It should be understood by one of ordinary skill in the art that the embodiment shown in FIGS. 3A-3C is provided merely for illustration, and to help understand the concepts which enhance the flexibility and conformity of a medical device. The number of cutouts, 316a and 316b, the dimensions of such cutouts, and the placement of the cutouts on the PCB 316 are preferably selected based on the specific number and layout of components in a particular embodiment and are not limited by the exemplary embodiment illustrated in FIG. 3A.

FIGS. 3A and 3B illustrate a flexible chassis 322 for use in exemplary embodiments of the present invention. For efficient operation of medical device 300, it is preferred that at least the reservoir 106, pump mechanism 114 and infusion needle deployment mechanism 108 all be located reasonably adjacent to each other. However, arranging such components too closely may result in an undesirable rigidity in the overall flexure of medical device 300. Flexible chassis 322, as shown in FIG. 3B, is provided to preferably house at least a low profile needle deployment mechanism 108 and pump mechanism 114. Chassis 322 comprises at least a first and second frame, 324 and 326, for holding the respective components in position relative to each other. A third optional frame 328 is shown, which in some embodiments may house a second needle deployment mechanism, a transcutaneous analyte sensor or biosensor, or any other components as will be understood by one of ordinary skill in the art. FIG. 3B illustrates how each of the respective frames, 324, 326 and 328, are maintained in relation to each other by flexible joints 322a molded to each of the connected frames. The interconnection of the system components using flexible joints 322a on chassis 322 serves to effectively hold the respective system components in relation to each other, while providing flexibility between the components of medical device 300. FIG. 3C is a cross section of medical device 300, illustrating the relative positioning and flexure of chassis 322 and PCB 316, in an exemplary embodiment of the present invention. One of ordinary skill in the art will appreciate that the relative dimensions and number of frames flexibly interconnected to each other are not limited by the illustrations in FIGS. 3A-3C, and are merely provided as examples.

Figure 5B:
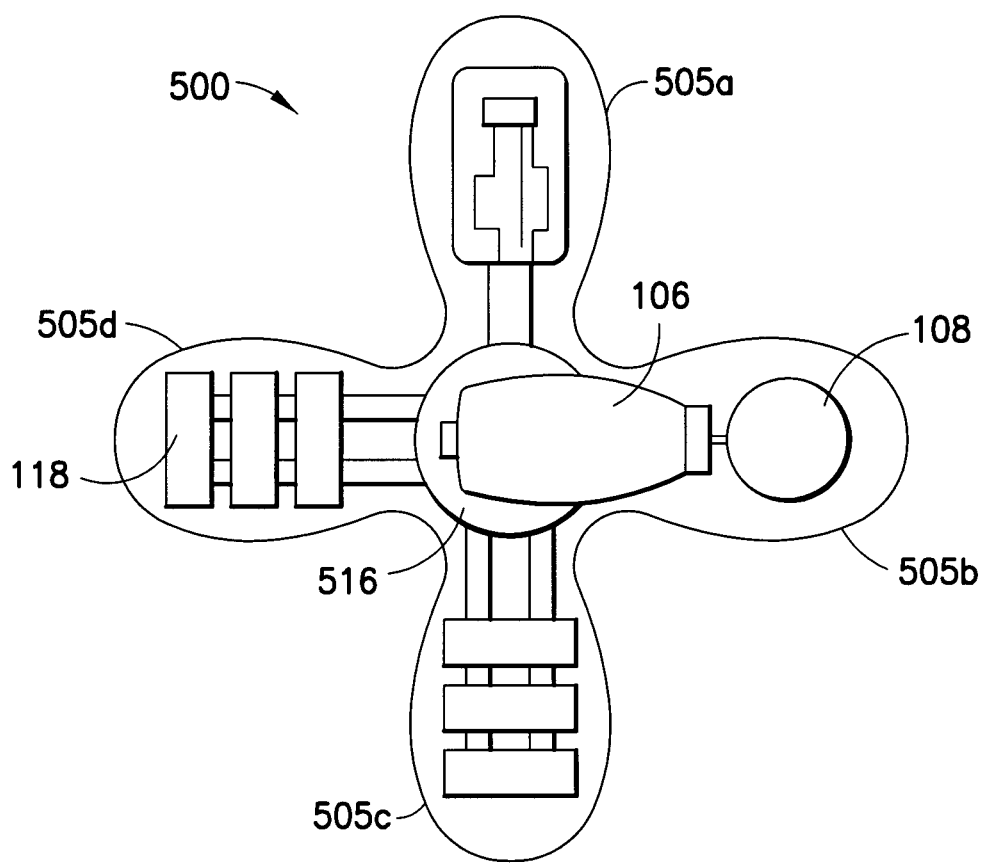
FIGS. 5A-5B illustrate a fourth exemplary embodiment of a medical device in accordance with an exemplary embodiment of the present invention.
Figure 4:
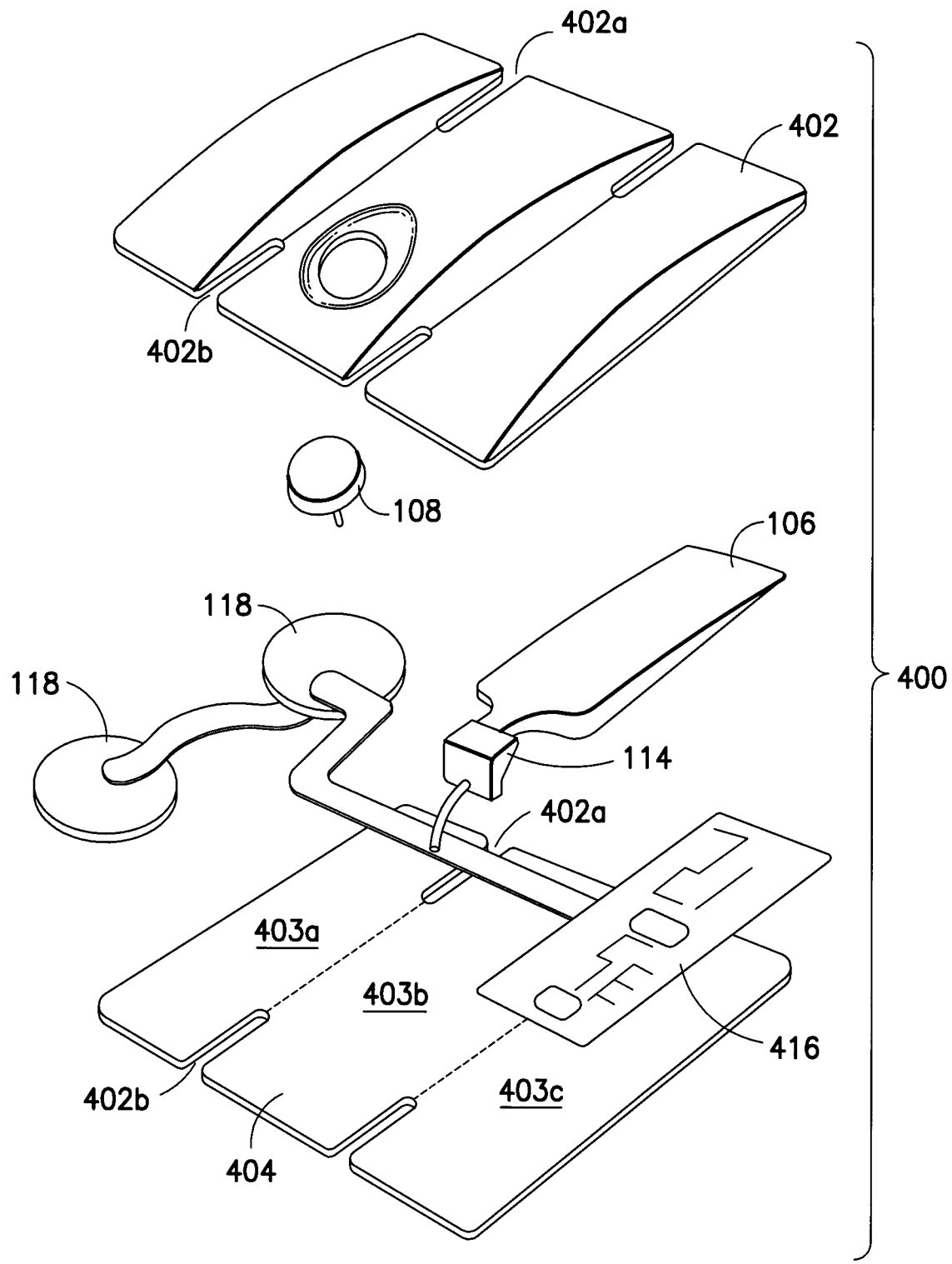
FIG. 4 is an illustration of a third exemplary embodiment of a medical device in accordance with an exemplary embodiment of the present invention.
Figure 5A:
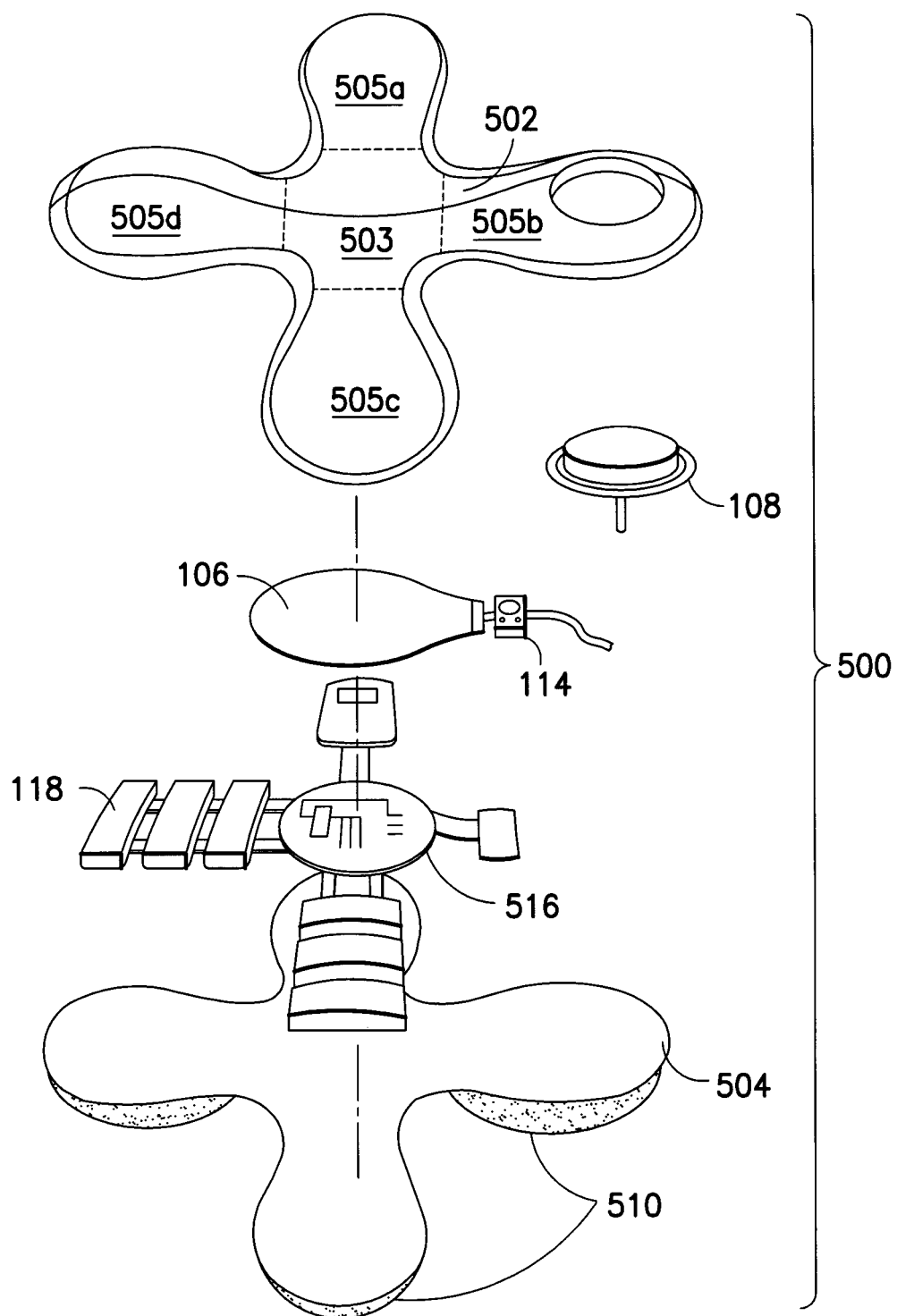

FIGS. 4 and 5A-5B illustrate third and fourth exemplary embodiments of a medical device 400 that provide additional degrees of flexibility for easily conforming to complex shapes. Similar to the modification of PCB 316 in FIG. 3, the flexible upper and lower covers of medical device 400, in an exemplary embodiment of the present invention, may be designed with slits, cutouts or recesses, 402a and 402b, along the perimeter of each. The number, size, and placement of recesses 402a and 402b illustrated in FIG. 4 is merely exemplary. The upper and lower covers, according to this exemplary embodiment, preferably comprise at least one inward extending recess 402a provided along the perimeter of each cover. The at least one recess is preferably but not necessarily provided with a second similar recess 402b at the opposite edge of the cover. The coordinating recesses preferably, effectively compartmentalize medical device 400, into modules 403a, 403b and 403c, and provide an added dimension of flexibility and conformity to the medical device for enabling a comfortable placement of medical device 400 on complex contours of a user's body.

The compartments or modules depicted in FIG. 4 preferably house at least one system component, such as the battery supply 118 in module 403a, flexible reservoir 106 and pump mechanism 114 in module 403b and flexible PCB 416 in module 403c. Ideally, but not necessarily, an entire component will be positioned inside a single compartment or module. By positioning the system components within the compartments, as illustrated in FIG. 4, preferably only a flexible connection extends from one compartment to the next. The area of greatest flexibility and conformity of medical devices 400 is where the individual compartments conjoin. Thus, by positioning the system components in the separate compartments, maximum flexibility and conformity of medical device 400 may be realized.

FIGS. 5A and 5B illustrate a fourth exemplary embodiment of a multi-dimensionally flexible medical device 500 that is also compartmentalized into modules or lobes and even further enhances the multi-dimensional conformity of the medical device. The upper and lower covers, 502 and 504, of medical device 500 preferably comprise a central "hub" area 503 of arbitrary shape and dimension with a plurality of modules or lobes 505a-505d, also of arbitrary shape, that extend radially from the central hub 503. Similar to the exemplary embodiment described in FIG. 4, medical device 500 preferably houses at least one system component in each of the lobes 505a-505d and the central hub 503. Ideally, but not necessarily, each lobe will entirely incorporate the system component positioned therein. Since medical device 500 is most flexible and conformal near the area where each of lobes 505a-505d conjoin the central hub area 503, it is preferred, where possible, that only a flexible connection extend from each lobe 505a-505d to the central hub 503. It is preferred, in exemplary embodiments of the present invention, that the specific components are arranged and shaped so as to adopt the overall or compartmental shape and mode of flexure of the upper and lower covers, such as the flexible PCB 516 shown in FIGS. 5A and 5B adopting the shape of central hub area 503, as well as flexible PCB 416 depicted in FIG. 4.

The specific components shown in FIGS. 5A-5B, as being contained within medical device 500, are provided only by example, and are not intended to be limiting. One of ordinary skill in the art will understand that the specific components and arrangement of components within the medical device 500 and especially within the individualized compartments will vary depending on the intended functionality of medical device 500. Any combination of components necessary for realizing a desired functionality of medical device 500 may be advantageously chosen and positioned within the flexible housing to achieve maximum flexibility and conformity of medical device 500. Additionally, the shape of upper and lower covers, 502 and 504, as shown in FIGS. 5A and 5B, is not limiting of exemplary embodiments of the present invention. One of ordinary skill in the art will understand that the device may be formed into any suitable shape that is flexible and conformal to the user's body.

The embodiment illustrated in FIG. 5A, provides an additional level of comfort for the user in addition to that achieved by the flexible design. As shown in FIG. 5A, lower cover 504 is preferably affixed to the user's skin with adhesive pads 510 provided on each of the radially extending lobes 505a-505d. In contrast, common patch pumps typically provide an adhesive layer that substantially covers the entire surface area of the portion of housing that is affixed to the user. Some user's skin may be particularly sensitive to the adhesive that is used and many users often find that it is somewhat painful to remove the medical device after a desired duration of use. Additionally, the adhesive layer used in common patch pumps does not enable the natural stretching or flexing of a user's skin in the area on which the adhesive is applied. Users often complain of discomfort from a feeling that their skin is being pulled as a result of the large surface area of the adhesive layer impeding the natural stretching and flexing of a user's skin. The separate adhesive pads 510, as shown in FIG. 5A, reduce the total surface area of the user's skin on which the adhesive is applied, and allow the user's skin between the pads to stretch more comfortably, thus minimizing any potential skin irritation and pain associated with the use of medical device 500.

Figure 5C:
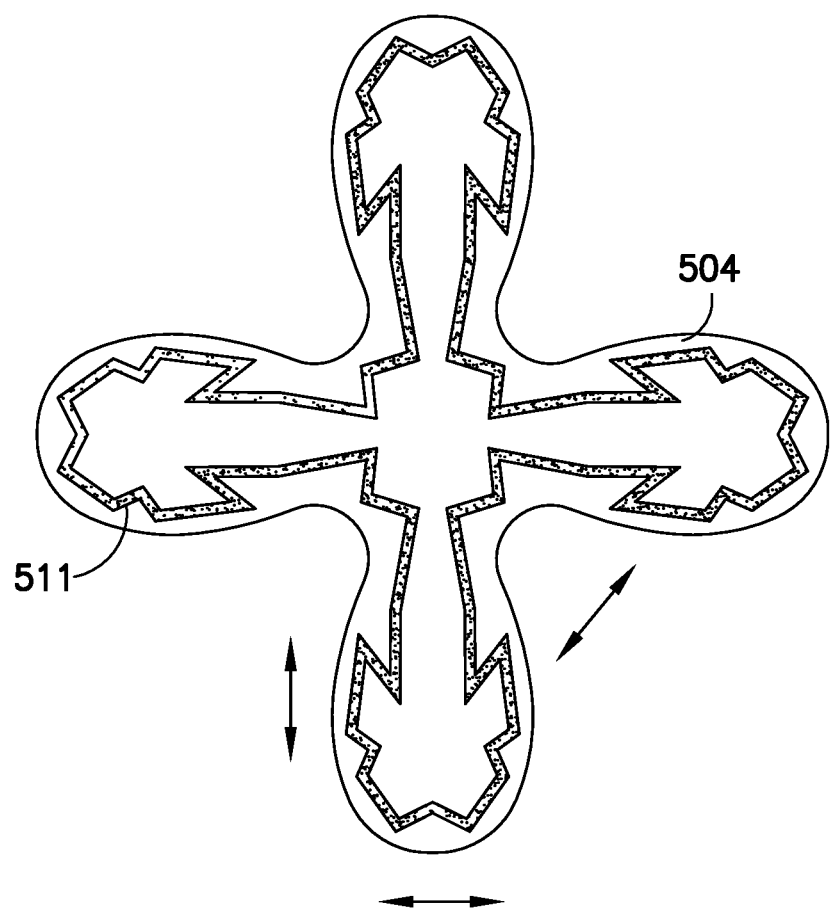
FIGS. 5C-5D illustrate an exemplary embodiment of an adhesive layer for use in any of the exemplary embodiments of a medical device.
Figure 5D:
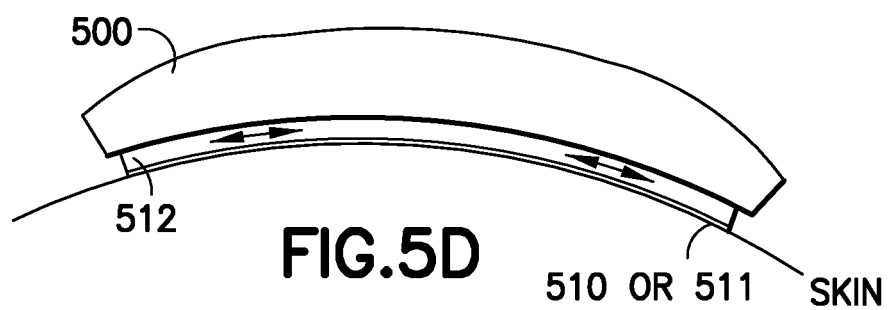

In other embodiments, the adhesive layer for use with exemplary embodiments of a medical device may adopt a pattern that enhances flexibility along the perimeter of the medical device for enabling increased freedom of movement at the interface of the user's skin and the exemplary medical device, such as a zig-zag pattern. For instance, a pattern 511 as shown in FIG. 5C for use with the medical device shown in FIG. 5, may be used in exemplary embodiments. A similar pattern may be adopted for use with any shape of the above described exemplary medical devices, as would be understood by one of ordinary skill in the art. Such a pattern reduces a user's awareness of the physical sensation accompanied by the adhesive interface and enables flexibility by allowing subtle movement to occur on the surface of the skin during normal physical activity. The adhesive layer is also preferably formed or formulated from a flexible material so as to enable subtle stretching of the adhesive layer, thus further enhancing comfort and flexibility of the medical device. It is preferred, that the freedom of movement provided by such an adhesive is subtle and should not cause undesirable movement at the infusion site. Nevertheless, in one embodiment, an additional non-flexible adhesive ring or perimeter, acting as an anchor, may be provided at the infusion site for preventing any undesirable movement at this site. Additional embodiments of the present invention may also comprise an adhesive layer of any desired shape or size with an increased thickness, or an elastomer or foam layer 512 sandwiched between the adhesive layer and the medical device, as shown in the side profile of medical device 500 depicted in FIG. 5D, for providing additional freedom of movement and flexibility. The thickness of layer 512 is preferably chosen to provide an increased overall flexibility of an exemplary medical device without overly increasing the profile of the medical device while affixed to the user's skin. The above embodiments are not limited to the medical device 500 as shown, but may be provided with any of the above exemplary medical devices.

The specific components and arrangement of the components that are depicted in FIGS. 2-5 are not meant to be limiting, and are provided to illustrate concepts of various embodiments of the present invention. Medical devices according to exemplary embodiments of the present invention may incorporate any combination of the components to be discussed below, as well as any other components available in the art for realizing specific functionality of a wearable medical device. The specific components are preferably provided in any advantageous arrangement for enabling a thin, flexible, conformal medical device, as will be understood by one of ordinary skill in the art.

Controller 116, as shown in FIG. 1, in an exemplary embodiment of the present invention, is provided at least for controlling pump mechanism 114 or a fluid metering device. Controller 116 is preferably an ultra low-power (ULP) programmable controller which combines the necessary processing power and peripheral set to control drug delivery through the pump mechanism 114, as well as to perform other optional system tasks, such as system or flow monitoring and communication with a host device or other external devices. Controller 116 is preferably embodied in an integrated circuit (IC) or a "system on a chip" (SoC) including any other circuitry, such as that necessary for communication with the host device. SoC designs usually consume less power and have a lower cost and higher reliability than the multi-chip systems that they replace. By providing a single chip system, overall size and area of the electronic components is reduced and the arrangement of such components is simplified.

The IC or SoC, in an exemplary embodiment of the present invention, is preferably provided on a flexible printed circuit board (PCB) 216, 316, 416 and 516 as shown in FIGS. 2-5, respectively. Flexible PCBs are well known in the art. The specific construction and specifications of such are outside the scope of the present disclosure. The flexible printed circuit boards preferably provide wiring and support for connecting leads of various electrical components to the controller 116 and power supply 118, such as pump mechanism 114, an automatic infusion needle mechanism 108, and an optional communication transceiver or blood glucose sensor, as well as any other electronic component. The flexible PCB, in each of the exemplary embodiments is preferably as flexible as the exemplary lower cover of the medical device, so as not to inhibit the overall flexibility of the medical device.

Power supply 118, in exemplary embodiments of the present invention, preferably comprises a thin flexible battery or batteries and/or supercapacitors. Flexible, thin supercapacitors and lithium-polymer batteries are well known in the art and are preferred in the exemplary embodiments of the present invention. Power supply 118 may comprise disposable or rechargeable power sources. One of ordinary skill in the art will appreciate that any known power supply that is thin and preferably flexible is suitable for providing a power supply 118 in exemplary embodiments of the present invention. In an alternative embodiment, a small rigid battery or batteries connected by flexible conductors may also be used. The embodiments of power supply 118 illustrated in FIGS. 2-5 are not limiting, and are provided merely to depict exemplary arrangements of a power supply in a medical device according to exemplary embodiments of the present invention. Power supply 118, in an alternative embodiment of the present invention, may be provided using energy harvesting techniques, alone or in combination with a standard power source, such as those disclosed in previously incorporated, co-pending U.S. patent application Ser. No. 12/458,807. Power supply 118 is preferably connected to the flexible PCB using flexible contacts. If multiple batteries are implemented, each of the batteries may be connected to each other using flexible contacts and are preferably spaced apart to promote optimum flexibility of medical device 100.

Reservoir 106 in the exemplary embodiments illustrated in FIGS. 2-5, comprises a flexible pouch or bladder for storing a drug or other therapeutic substance for delivery to the user. In an exemplary embodiment, reservoir 106 is provided to the user pre-filled. Reservoir 106 is preferably constructed from a flexible polymer that is compatible with the drug or substance to be stored therein. Various shapes and dimensions of reservoir 106 are shown in FIGS. 2-5. One of ordinary skill in the art will understand that the specific illustrations are not limiting, and the design of reservoir 106 may be altered depending on the specific embodiment of medical device 100. Reservoir 106 is preferably designed to be low-profile, so as to achieve a reduced overall height/thickness of medical device 100. Reservoir 106 in the exemplary embodiments preferably holds a volume of drug that is sufficient for the intended duration of use of the medical device. In some cases, however, a large required volume of drug may be prohibitive to an exemplary thin medical device. Alternate embodiments may include a fill port and septum provided on the upper cover for enabling a user to refill reservoir 106, such as with a prefilled or fillable syringe, so as to enable a reduced surface area of the reservoir 106. In these embodiments, reservoir 106 may also be fillable by the user prior to use.

Common patch pumps available in the art typically include a rigid cylindrical tube as a reservoir for housing a drug and comprise a mechanism for displacing the volume within the reservoir to provide the drug to a pumping or infusion mechanism, similar to a syringe and plunger or piston. Flexible reservoir 106 in the exemplary embodiments of the present invention, however, introduces a unique challenge for supplying the drug to the user, as the drug cannot be displaced from the reservoir using common techniques. As such, exemplary embodiments of the present invention employ pumping mechanisms or fluid metering devices that are capable of drawing a fluid or drug from a flexible reservoir 106.

Figure 6A:
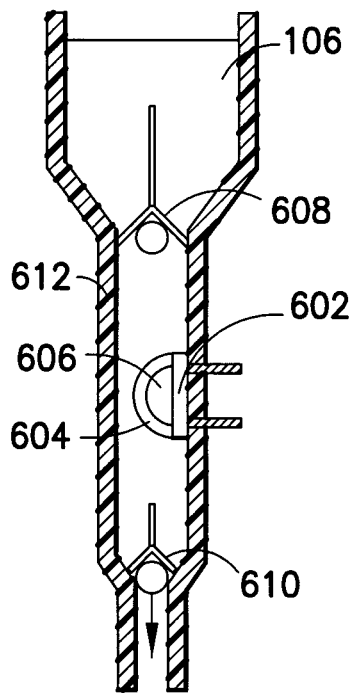
FIGS. 6A-6C illustrate an exemplary embodiment of a pump mechanism for use in any of the exemplary embodiments of a medical device.
Figure 6B:
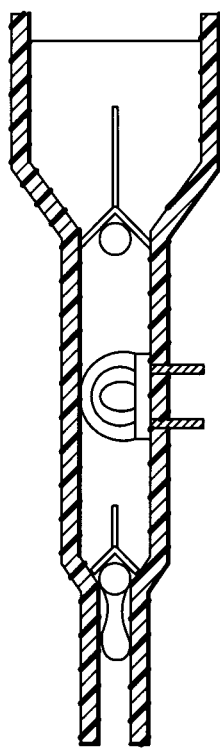
Figure 6C:
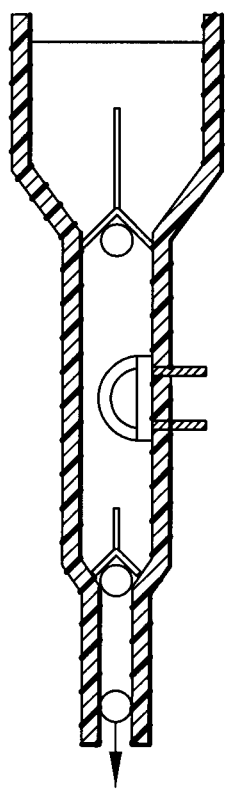

A first exemplary pump mechanism 614 or fluid metering device for use in exemplary embodiments of the present invention comprises a "thermal bubble micro pump", as shown in FIGS. 6A-6C. A thermal resistor 602 is provided near the distal end of a flow chamber 612 connected to reservoir 106. Thermal resistor 602 generates heat from an electrical current selectively passed therethrough, which vaporizes a thermal expansion fluid 606, generating a gas bubble and expanding flexible membrane 604. Flexible membrane 604 expands into the narrow flow chamber 612 forcing a drop of a drug to the cannula, as shown in FIG. 6B. As the drop of the drug is separated from the main body of fluid, thermal expansion fluid 606 cools and condenses, thus flexible membrane 604 reverts back to its original state shown in FIGS. 6A and 6C. As flexible membrane 604 relaxes to its original state, an additional volume of drug from reservoir 106 is drawn into the narrow flow chamber 612. This embodiment may also include at least one optional one-way check valve within flow chamber 612 for controlling displacement of the drug in the flow chamber. A first one-way check valve 608 is preferably provided in flow chamber 612 between reservoir 106 and the thermal resistor 602. This one-way check valve serves to block the flow of drug back into reservoir 106 when flexible membrane 604 expands, as discussed above. A second optional one-way check valve 610 may be placed between thermal resistor 602 and the infusion cannula. The second one-way check valve permits the flow of the drug only in one direction, to the user. The one-way check valve 610 inhibits a flow of drug back into flow chamber 612 as flexible membrane 604 retracts. Each of the optional one-way check valves may be substituted with an electronically controlled gate or valve or any other suitable mechanism for controlling the delivery of drug to the user, as would be appreciated by one of ordinary skill in the art. The above process may be repeated indefinitely. The frequency of expansion of flexible membrane 604 and the dimensions of the flow chamber can be controlled and designed to achieve a desired flow rate of drug to the user.

The process of vaporizing the thermal expansion fluid and then condensing the expansion fluid makes up a complete expansion/contraction cycle necessary for expelling and drawing in a volume of the drug. When using a single thermal resistor as shown in FIGS. 6A-6C, if continuous infusion is required, the cooling/condensing process of the cycle must be accelerated. As such, an optional heat sink or heat pipe (not shown) may be provided for facilitating the condensing of the thermal expansion fluid. Any heat sink or heat pipe known in the art that is suitable for use in the present invention may be provided, as would be appreciated by one of ordinary skill in the art.

Another embodiment may be provided with a plurality of thermal expansion units placed in sequence within flow chamber 612 to effect a peristaltic type pump operation for controlling the flow of drug to the user, as shown in FIGS. 6D-6H. The operation of this embodiment is similar to that discussed above with respect to FIGS. 6A-6B, except in this embodiment an electrical current is passed sequentially to thermal resistors 602a, 602b and 602c. An electrical current first provided to thermal resistor 602a results in the expansion of flexible membrane 604a thus forcing a volume of drug toward the cannula. An electrical current is then subsequently provided to the second thermal resistor 602b which results in the expansion of flexible membrane 604b and further movement of a volume of drug toward the cannula. Next, an electrical current provided to thermal resistor 602c results in the expansion of thermal membrane 604c and expulsion of a volume of drug from flow chamber 612 into the cannula. By sequentially applying a current to each thermal resistor, the pattern of expansion of the thermal membranes ensures that the drug will move in the intended direction. This process is shown in the sequence of FIGS. 6E-6H. As the electrical current is removed from each of the thermal resistors in sequence, the respective thermal expansion fluid condenses and reverts back to the original volume, thus enabling an additional volume of drug to replace the expelled volume. Since a plurality of thermal resistors are provided in sequence, as the "down stream" thermal resistors are charged, the previously charged resistors begin to cool and condense the thermal expansion fluid. As such, a previously charged thermal resistor has more time to cool and condense the thermal expansion fluid, thus enabling a continuous expansion/contraction cycle for effecting a continuous flow of drug to the user.

It should be appreciated by one of ordinary skill in the art, that the thermal expansion membranes 604 shown in FIGS. 6A-6H do not need to be integral with or contained inside flow chamber 612. It may also be preferable to provide the thermal expansion membranes separate and adjacent to flow chamber 612, so as to "pinch" the flow chamber upon expansion. Pinching flow chamber 612 in this manner acts in a similar fashion to facilitate flow of the drug from the reservoir 106 to the cannula at the infusion site.

Figure 6D:
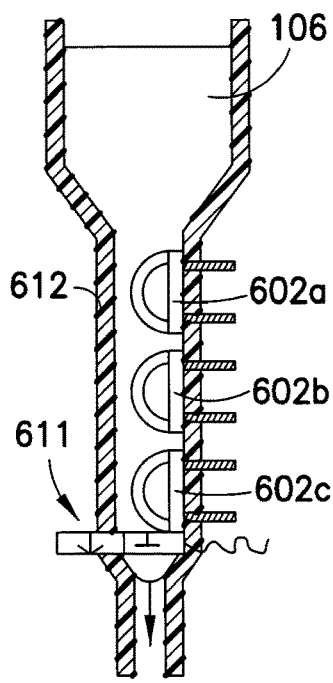
FIGS. 6D-6H illustrate an additional exemplary embodiment of the pump mechanism shown in FIGS. 6A-6C for use in any of the exemplary embodiments of a medical device.
Figure 6E:
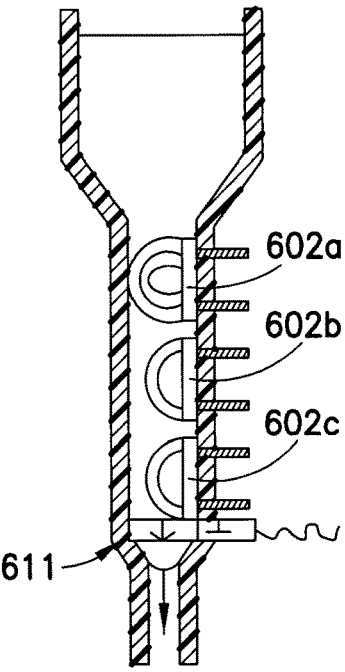
Figure 6F:
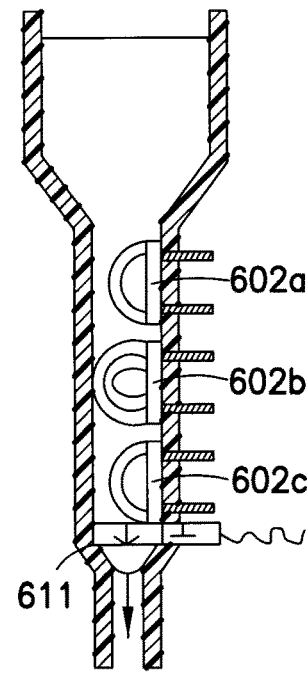
Figure 6G:
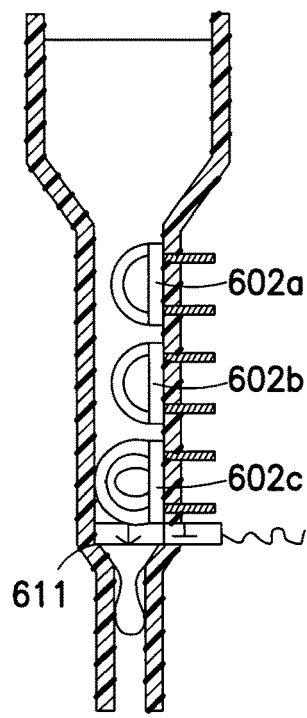
Figure 6H:
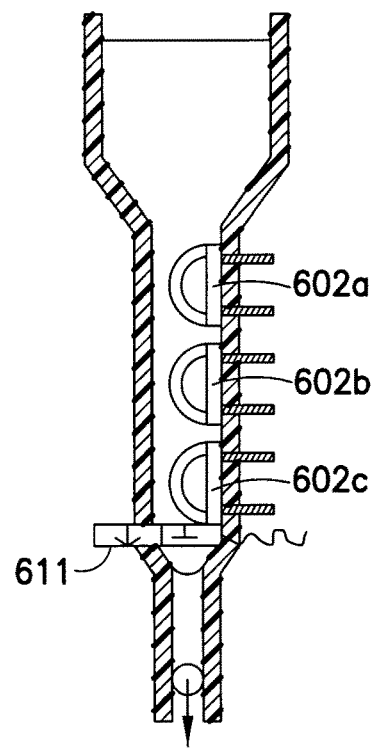

A one-way electronic gate 611 is shown for controlling the flow of drug to the user. In FIG. 6D, electronic gate 611 is shown as controlled in a state for preventing drug flow from entering the cannula. As an electrical current is sequentially provided to thermal resistors 602a-602c, electronic gate 611 is controlled to enable the flow of drug to the cannula, as shown in FIGS. 6E-6G. Once the volume of drug is expelled to the cannula, electronic gate 611 can be controlled to prevent the expelled volume of drug from being drawn back into flow chamber 612, as shown in FIG. 6H. The electronic gate 611 may be substituted with a one-way check valve similarly provided in FIGS. 6A-6C or any other means for controlling the flow of drug to the user, as would be appreciated by one of ordinary skill in the art.

Figure 7:
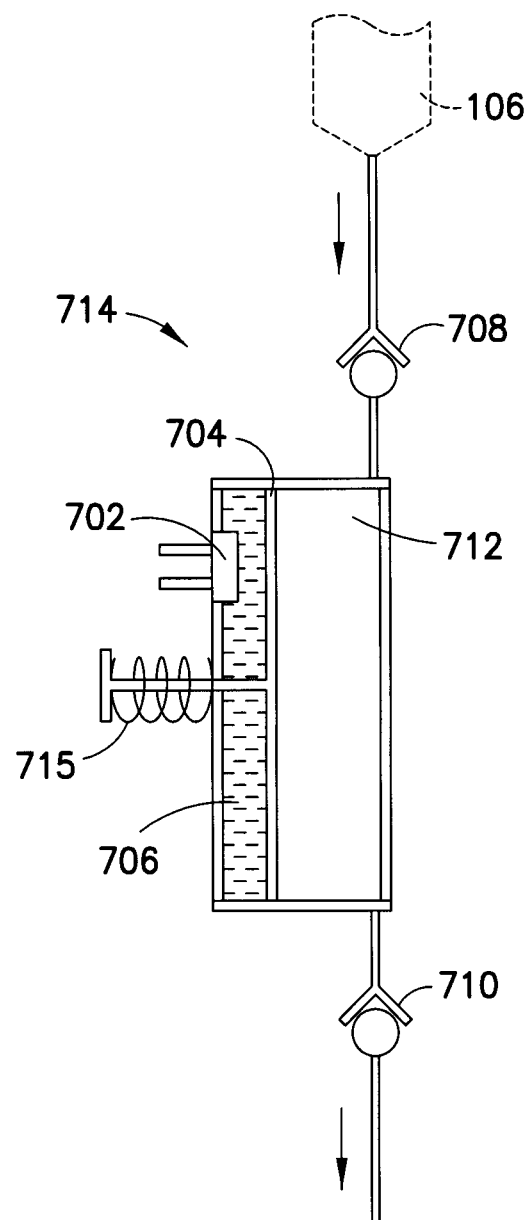
FIG. 7 illustrates another exemplary embodiment of a pump mechanism for use in any of the exemplary embodiments of a medical device.

A second exemplary pump mechanism 714 using a similar concept described above, is illustrated in FIG. 7. In this embodiment, a holding chamber 712 temporarily houses a volume of the drug to be delivered to the user, such as a bolus dose of insulin. The volume of drug enters holding chamber 712 from reservoir 106 through a one way check valve 708. As an electric current is applied to thermal resistor 702, thermal expansion fluid 706 is heated and expands, driving diaphragm 704 towards holding chamber 712, thereby displacing the volume of drug in holding chamber 712 and forcing the drug through a second one way check valve 710 to the delivery cannula. The one way functionality of reservoir-side check valve 708 prevents the drug from being forced back into reservoir 106. Once thermal expansion fluid 706 cools and condenses, the force applied by spring 715 is sufficient to drive diaphragm 704 away from holding chamber 712, thereby increasing the volume of holding chamber 712, which draws an additional drug volume into holding chamber 712 from reservoir 106. The cannula-side check valve 710 prevents the drug in the cannula from being drawn back into holding chamber 712. As would be appreciated by one of ordinary skill in the art, one way check valves 708 and 710 may be substituted with an electronically controlled gate such as that shown in FIGS. 6D-6H and FIG. 9 or any other suitable means for controlling the flow of drug to the user.

The above process may repeat indefinitely and may be controlled to provide a desired flow rate of the drug to the user. The volume of drug delivered to the user is equivalent to the volume of drug that is displaced from holding chamber 712. The capacity of holding chamber 712 and the amount of displacement caused by thermal expansion fluid 706 can be designed and controlled to provide a desired infusion rate of the drug to the user. In a modified embodiment of the system illustrated in FIG. 7, the thermal resistor and thermal expansion fluid may be replaced with a solenoid shaft acting as a piston to control fluid displacement in holding chamber 712.

Figure 8:
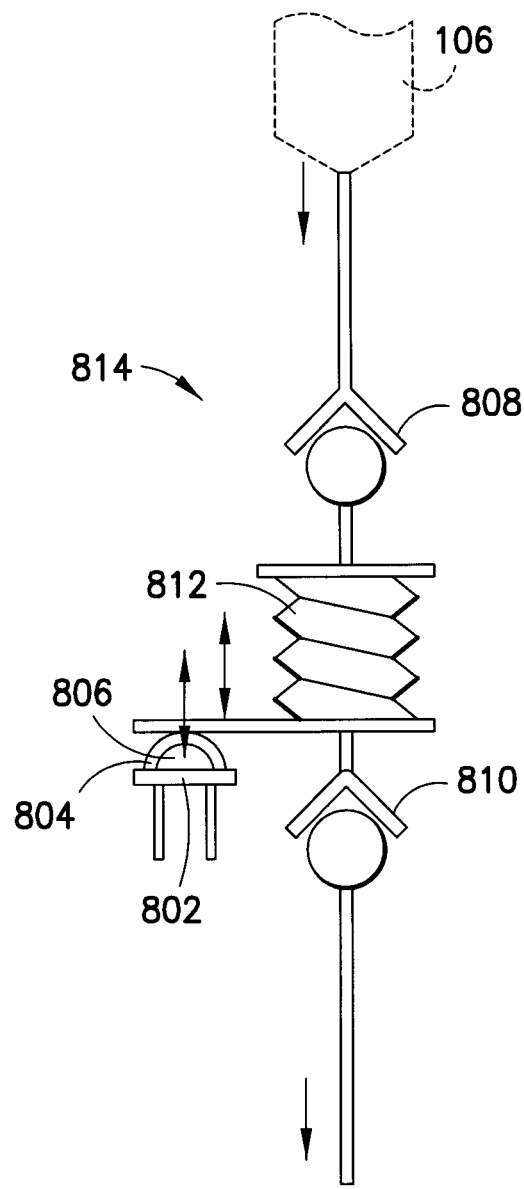
FIG. 8 illustrates a third exemplary embodiment of a pump mechanism for use in any of the exemplary embodiments of a medical device.

FIG. 8 illustrates a third exemplary pump mechanism 814 using similar concepts as above. This embodiment utilizes a bellows fluid chamber 812 that expands when drawing in a drug and compresses to expel the drug from the chamber. The expansion and compression of bellows chamber 812 is driven by a thermal resistor 802 and thermal expansion fluid 806. When applied with an electric current, thermal resistor 802 heats thermal expansion fluid 806 which vaporizes, expanding substantially, and applies a force to flexible membrane 804. The force imparted on flexible membrane 804 causes the membrane to expand, thus driving the bellows chamber 812 to a compressed state and expelling a volume of drug through one-way check valve 810. As the electric current is removed from thermal resistor 802, thermal expansion fluid 806 condenses and alleviates the force on flexible membrane 804. As flexible membrane 804 relaxes to its original state, bellows chamber 812 is pulled downward, as illustrated in FIG. 8, to an expanded state, thus drawing in an additional volume of drug from reservoir 106 to be supplied to the user as desired.

Figure 9:
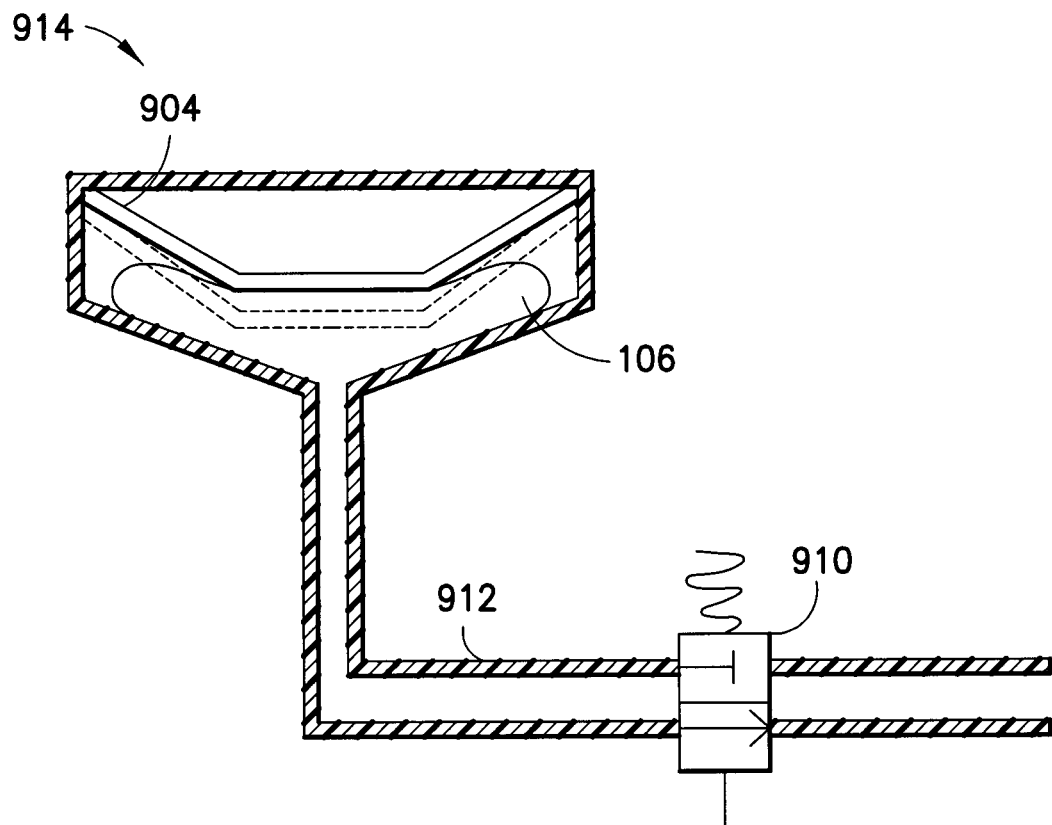
FIG. 9 illustrates a fourth exemplary embodiment of a pump mechanism for use in any of the exemplary embodiments of a medical device.

Another exemplary pump mechanism 914 suitable for use in the present invention is illustrated in FIG. 9. This embodiment uses a Belleville spring 904 or other suitable spring mechanism, such as a stamped leaf spring, snap acting disk or flexure, to apply a force to flexible reservoir 106. The pressure applied by the Belleville spring urges the drug of reservoir 106 into a flow chamber 912. The pressurized drug is blocked from infusion into the user by an electronically controlled gate or metering valve 910, such as a solenoid controlled two-way fluidic valve. Metering valve 910 is preferably controlled by controller 116 to enable a desired rate of drug flow to the user. Any metering valve or gate that may be electronically controlled to enable a desired rate of flow would be suitable in this embodiment of the present invention, as will be understood by one of ordinary skill in the art, such as a ferrofluidic gate or valve.

Figure 10:
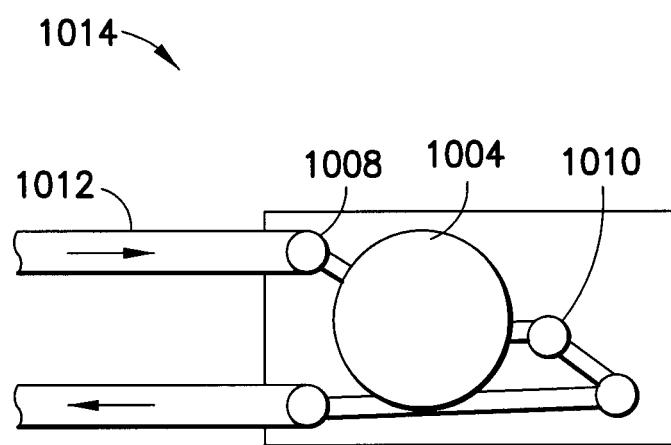
FIG. 10 illustrates a fifth exemplary embodiment of a pump mechanism for use in any of the exemplary embodiments of a medical device.

An additional exemplary pump mechanism 1014, for use in exemplary embodiments of the present invention, comprises a simple diaphragm pump, as shown in FIG. 10, that draws a drug from a flexible reservoir (not shown). The diaphragm pump shown in FIG. 10 may be provided as a MEMS nanopump, available from Debiotech S.A., and generally comprises a series of check valves 1008 and 1010 and a piezoelectric diaphragm 1004 for realizing the flow of a drug or other substance housed in the reservoir. Piezoelectric diaphragm 1004 is positioned in the flow channel 1012 and changes a size and shape to a deformed state in the presence of an applied voltage. Diaphragm 1004 can be controlled to repeatedly switch from an undeformed state to a deformed state. This repeated action functions as a pump to draw in a drug from reservoir 106 through the first one-way check valve 1008 and expel the drug through the second one-way check valve 1010.

Other alternative pumping mechanisms and fluid metering devices may also be used in other embodiments of the present invention. One of ordinary skill in the art will find it reasonable to implement any known pump mechanism suitable in a wearable medical device for dispensing a liquid medicament/drug to a user. Regardless of the chosen mechanism, it is preferable that the pump mechanism be compact, lightweight, and low-profile, so as not to unnecessarily increase the size and thickness of the medical device.

The exemplary embodiments of the medical devices illustrated in FIGS. 2-5 include a low-profile needle deployment mechanism 108 that may be manually or automatically actuated for inserting an infusion cannula into the user. The infusion cannula for use in the exemplary embodiments of the present invention may comprise an infusion needle with a side port for infusing the drug into the user or may alternatively comprise a flexible cannula inserted into the user with the aid of an insertion needle. Additionally, a flexible cannula may be provided with a sharpened tip to enable insertion of the flexible cannula into the user, thereby eliminating the need for a separate insertion needle. The tip may optionally be hardened relative to the shaft. Other additional exemplary embodiments may comprise an in-dwelling flexible, slotted steel needle or a highly flexible torsion spring preferably provided with a sharpened needle tip attached. Each of the slotted steel needle and torsion spring embodiments is also preferably encased in a Teflon® or Vialon® sheath or coating for sealing a fluid flow chamber within. More detailed descriptions may be found in co-pending commonly owned U.S. Patent Application titled "Extended Use Medical Device", filed on even date herewith, which is hereby incorporated by reference in its entirety. Of course any suitable fluid tight material could be used to form the sheath. The slotted steel needle and torsion spring embodiments are flexible for increased comfort, yet provide a rigidity or column strength necessary for insertion into the user's skin. The slotted steel needle is made flexible due to the slots, and advantageously need not have a separate tip, but rather can be a unitary body having a sharpened tip. The torsion spring preferably includes a separate sharpened tip attached to penetrate the user's skin. Another exemplary embodiment of the present invention utilizes an array of micro-needles such as those implemented in Nanoject, an infusion device provided by Debiotech S.A. Any other suitable infusion mechanism may be used in the exemplary embodiments of the present invention, as will be appreciated by one of ordinary skill in the art.

Figure 11A:
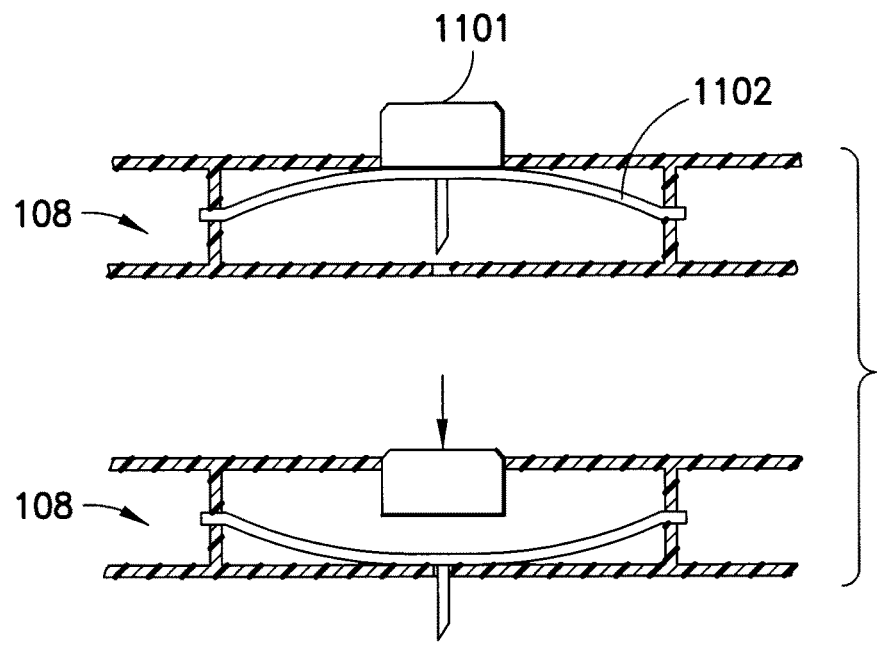
FIGS. 11A-11E illustrate exemplary embodiments of a needle deployment mechanism for use in any of the exemplary embodiments of a medical device.
Figure 11B:
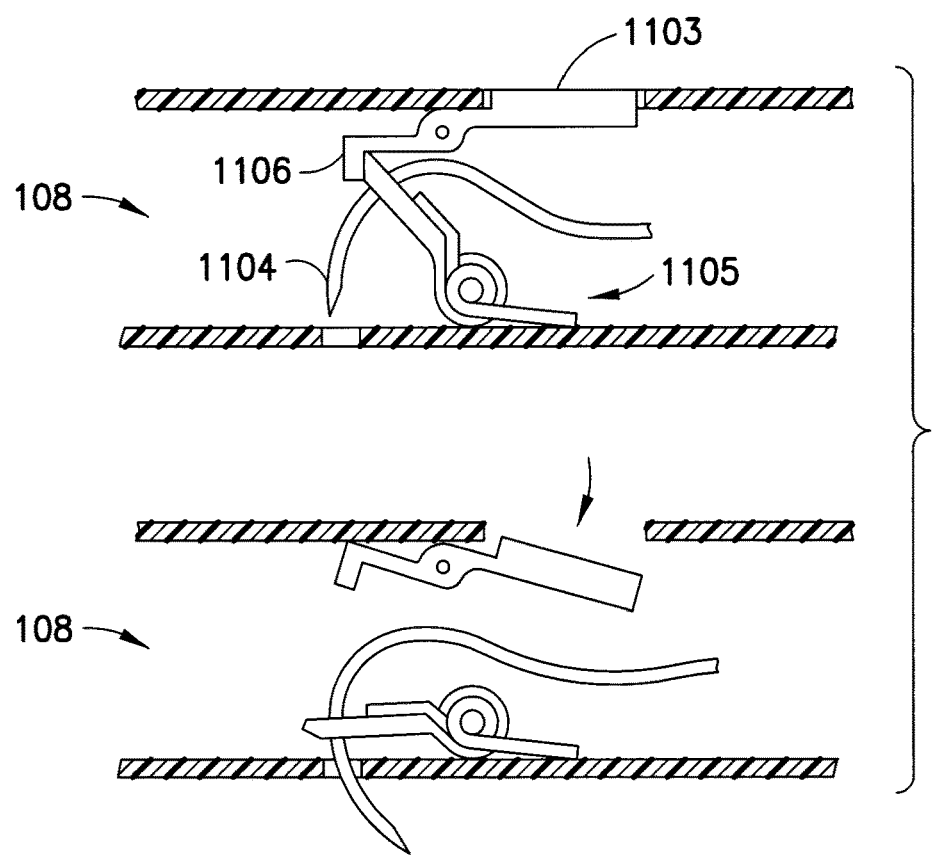

FIGS. 11A-11E and FIGS. 12A-12D illustrate exemplary embodiments of a needle deployment mechanism 108 for use in exemplary embodiments of the present invention. FIG. 11A illustrates a manually actuated snap disk 1102 for inserting an infusion needle or cannula into the user. A force applied to button 1101 urges snap disk 1102 from a convex position to a concave position, driving the infusion cannula into the user. A second exemplary embodiment of needle deployment mechanism 108, illustrated in FIG. 11B, uses a torsion spring 1105 for driving an infusion cannula into the user. The infusion cannula in this embodiment comprises a circular formed needle 1104. Circular formed needle 1104 is constrained to a circular path guided by torsion spring 1105. Prior to actuation, the needle is held in a ready position by a blocking arm 1106 attached to a finger lever 1103. A user actuates needle deployment in this embodiment by applying a force to an end of finger lever 1103 opposite blocking arm 1106. When the user applies a downward force to lever 1103, blocking arm 1106 of the lever pivots away from a blocking position and enables torsion spring 1105 to drive the infusion needle into the user.

Figure 11C:
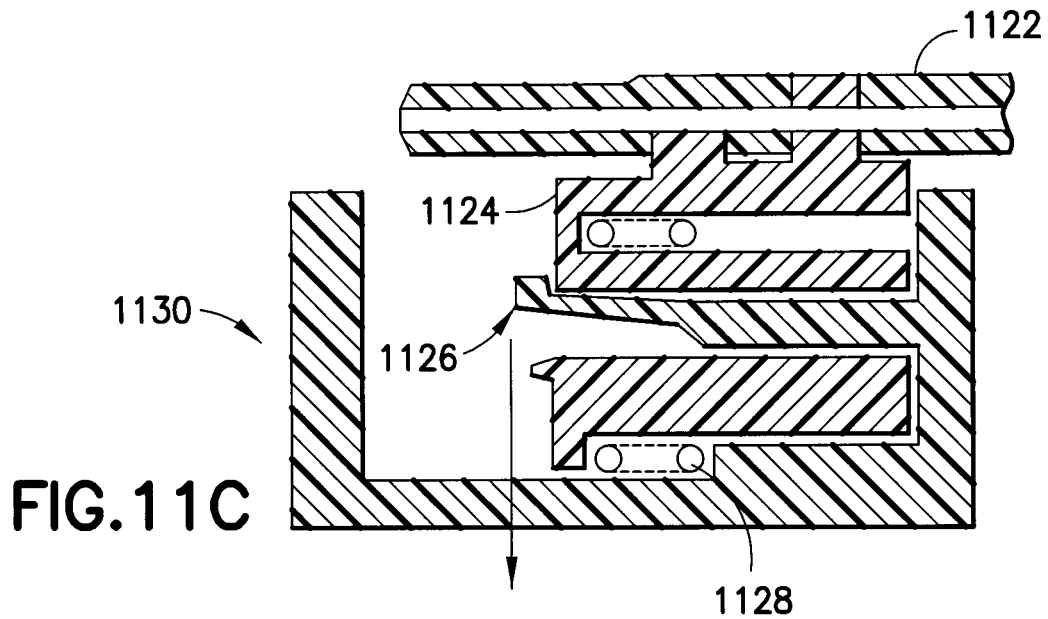
Figure 11D:
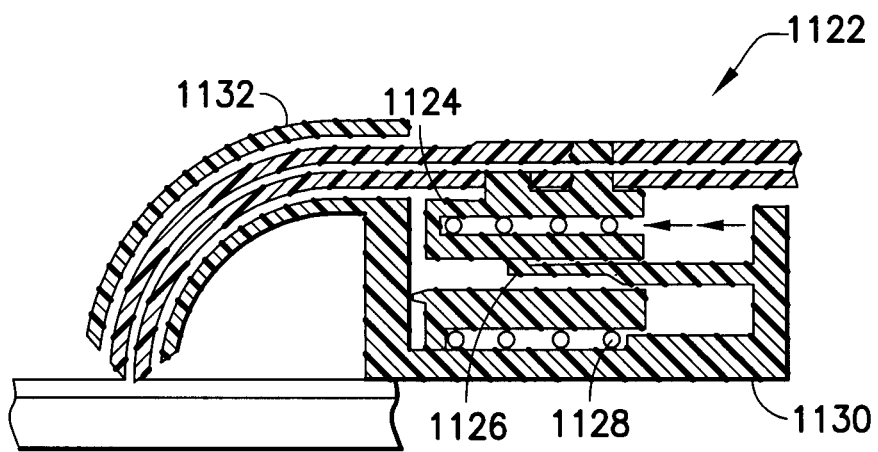
Figure 11E:
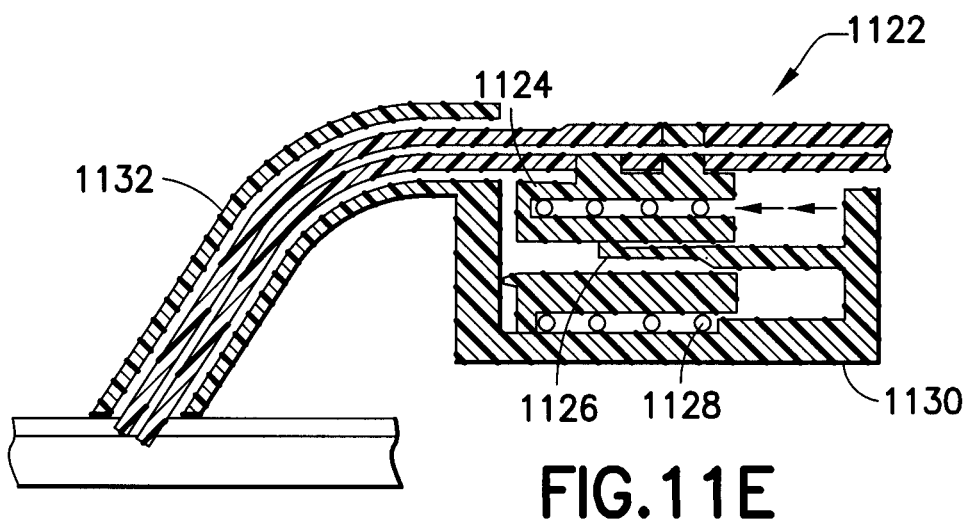

FIGS. 11C-11E illustrate another exemplary embodiment for use in the present invention that is especially suitable for the flexible, slotted steel and torsion spring infusion needles discussed above. As shown in FIG. 11C, a flexible infusion needle 1122 is attached to a needle carriage 1124. Needle carriage 1124 is held in a retracted, ready position by a retention latch member 1126, which prevents needle carriage 1124 from movement in the insertion direction. Infusion needle deployment may be actuated manually or automatically to displace the retention latch member 1126 from a blocking position. When retention latch 1126 is actuated, a compression spring 1128 drives needle carriage 1124 in an insertion direction, as shown in FIG. 11D. After infusion needle 1122 is inserted into the user, distal movement of needle carriage 1124 is impeded by a chassis 1130 or housing containing the needle deployment mechanism. FIGS. 11D and 11E illustrate the needle deployment mechanism of FIG. 11C with a guide sleeve 1132 for guiding the flexible infusion needle 1122 into the user at a desired insertion angle. Additionally, guide sleeve 1132 provides additional integrity for the flexible needle 1122 so as to resist kinking or other undesirable deflection during deployment. As should be appreciated from FIGS. 11D and 11E, guide sleeve 1132 can be configured within the medical device to enable deployment in various orientations with respect to the motion of needle carriage 1124. As such, the use of guide sleeve 1132 in the exemplary embodiments enables deployment of infusion needle 1122 into the skin while minimizing the affect of the needle deployment mechanism on the overall profile of the medical device, by permitting the carriages to move parallel to the skin.

Figure 12A:
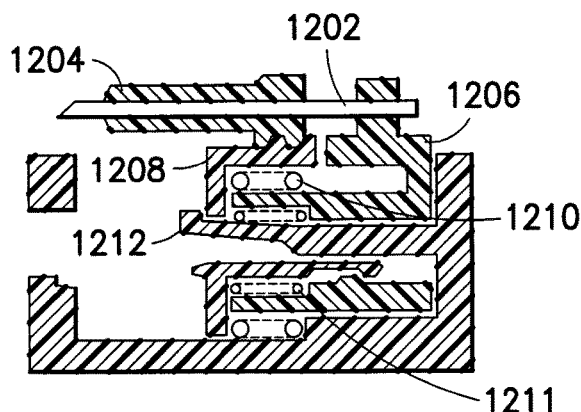
FIGS. 12A-12D illustrate another exemplary embodiment of a needle deployment mechanism for use in any of the exemplary embodiments of a medical device.
Figure 12B:
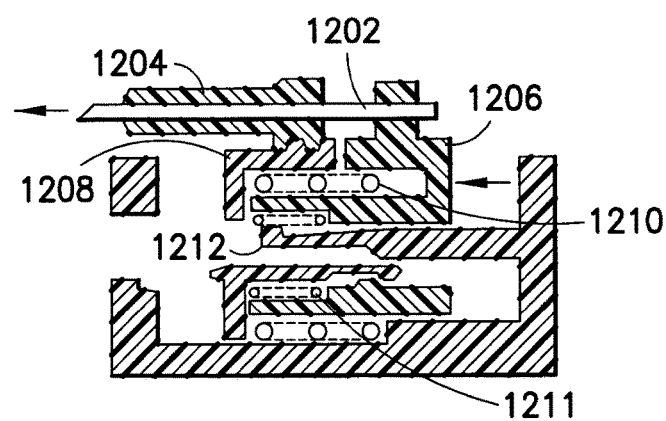
Figure 12C:
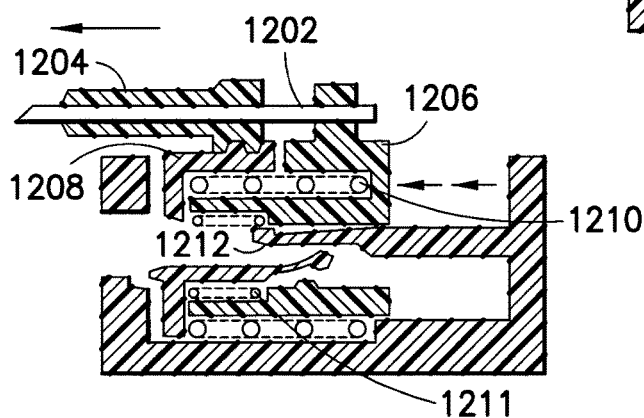
Figure 12D:
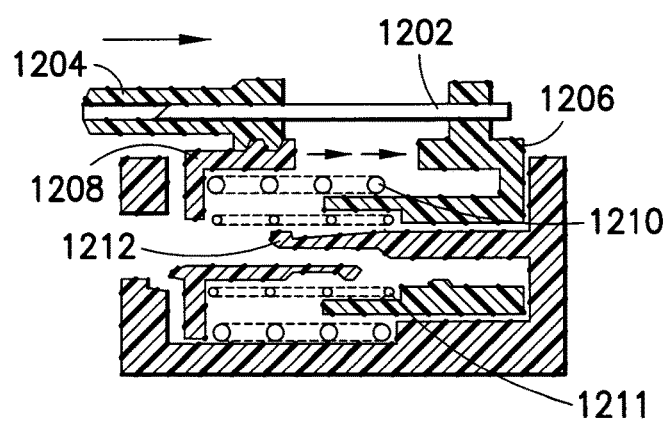

FIGS. 12A-12D illustrate an exemplary embodiment of a needle deployment mechanism similar to that described above with respect to FIG. 11C, for automatically or manually driving a flexible cannula into a user with the aid of an insertion needle. As shown in FIG. 12A, rigid insertion needle 1202 is provided in the inner cavity of a flexible cannula 1204, with a sharpened tip extending from the end of the flexible cannula 1204. The insertion needle and cannula are held in relative position to each other by needle carriage 1206 and cannula carriage 1208. Needle carriage 1206 and cannula carriage 1208 are held in a retracted, ready position by a retention latch member 1212, which blocks cannula carriage 1208 from movement in the insertion direction. Needle deployment may be actuated manually or automatically to displace the retention latch member 1212 from a blocking position. When retention latch 1212 is actuated, a first compression spring 1210 drives cannula carriage 1208 in an insertion direction, as shown in FIG. 12B. Needle carriage 1206 is engaged with cannula carriage 1208, thus the insertion motion of cannula carriage 1208 drives needle 1202 into the user. After needle 1202 and cannula 1204 are inserted into the user, distal movement of cannula carriage 1208 is impeded by a chassis or housing containing the needle deployment mechanism. As shown in FIG. 12C, at the point when distal movement of cannula carriage is impeded, cannula carriage 1208 and needle carriage 1206 become disengaged. At this point, a second compression spring 1211 drives the disengaged needle carriage 1206 in a proximal direction, thus withdrawing needle 1202 from the user while cannula 1204 remains inserted, as shown in FIG. 12D.

In the exemplary embodiments discussed above, a user may manually actuate insertion of the cannula by asserting a force onto the actuation button, finger lever or other latch retention means provided on the external surface of the upper cover, as shown in FIGS. 2, 4 and 5A. Additionally, because of the thin flexible nature of the upper cover of medical device 100 in each of the embodiments discussed above, the manual actuation means may be provided within the housing and are preferably actuated by applying a force to a specific area on the external surface of the upper cover.

The above needle deployment mechanisms are provided as exemplary embodiments only. The embodiments shown in FIGS. 11 and 12 may also utilize motorized components or other electrical components, instead of the latch and spring mechanisms, for deploying an infusion cannula into a user. One of ordinary skill in the art will understand that any needle deployment mechanism available in the art may be implemented in alternate embodiments of the present invention. It is preferable that the chosen needle mechanism comprises a relatively simple structure and be low-profile so as to realize a thin, flexible medical device.

Figure 12E:
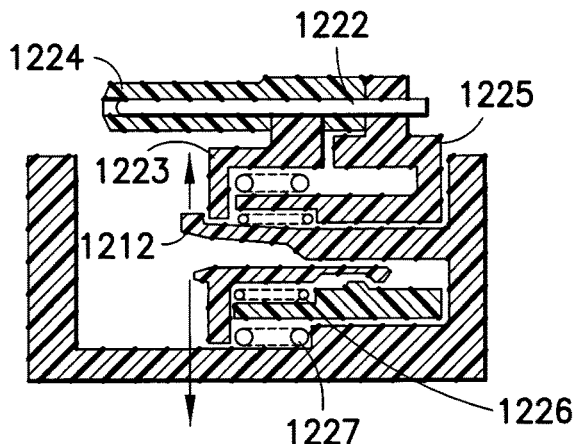
FIGS. 12E-12H illustrate an exemplary embodiment of a sensor deployment mechanism for use in any of the exemplary embodiments of a medical device.
Figure 12F:
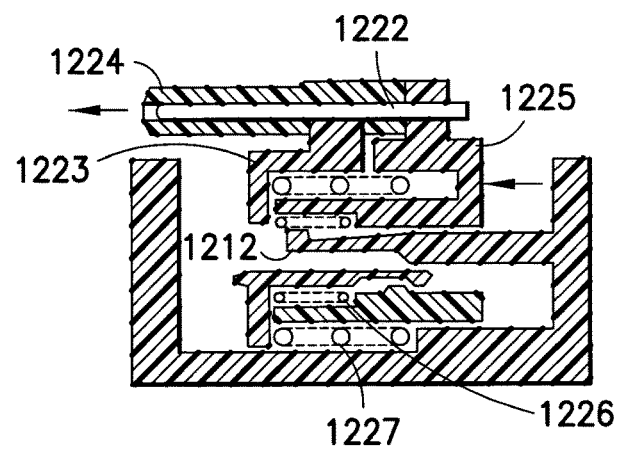
Figure 12G:
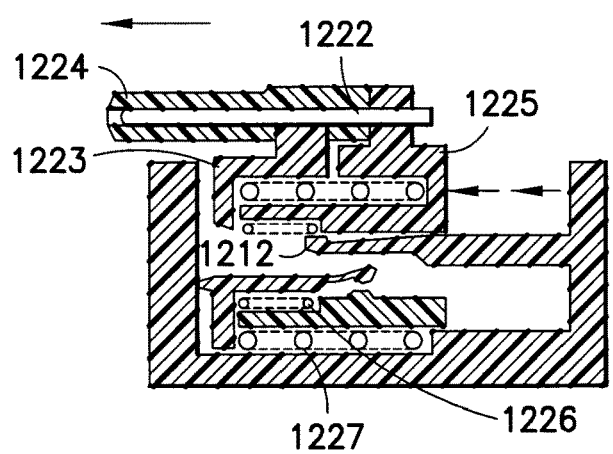
Figure 12H:
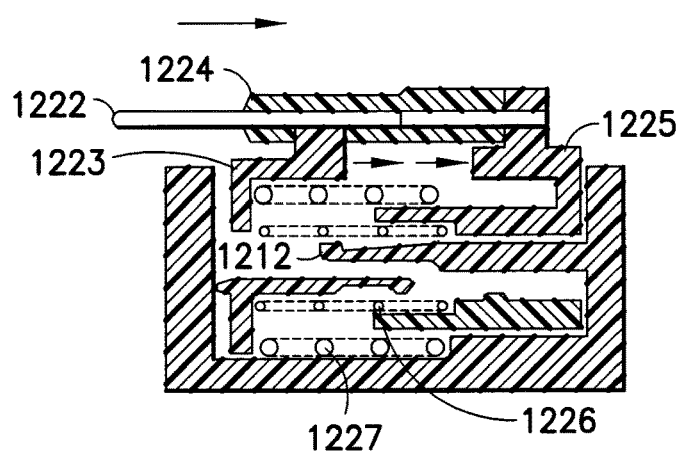

Additionally, any of the above needle deployment mechanisms may be slightly modified for deploying a transcutaneous analyte sensor or biosensor, such as a blood glucose sensor, for use in alternate embodiments of medical device 100 for realizing continuous blood glucose monitoring, as will be understood by one of ordinary skill in the art. For instance, the embodiment described in FIGS. 12A-12D may be provided for inserting a biosensor 1222 positioned internal to an outer sleeve or needle 1224 as shown in FIGS. 12E-12H. After deployment of the biosensor 1222, the outer sleeve 1224 may retract, leaving the biosensor 1222 exposed in the subcutaneous tissue of the user. As shown in FIG. 12E, the biosensor 1222 and needle 1224 are held in relative position to each other by needle carriage 1225 and biosensor carriage 1223. Needle carriage 1225 and biosensor carriage 1223 are held in a retracted, ready position by a retention latch member 1212, which blocks biosensor carriage 1223 from movement in the insertion direction. Sensor deployment may be actuated manually or automatically to displace the retention latch member 1212 from a blocking position. Of course it should be understood that deployment may be caused by manual deployment, or electronically via an appropriate command received from a BGM or host device. When retention latch 1212 is actuated, a first compression spring 1226 drives the needle carriage 1225 and biosensor carriage 1223 in an insertion direction, as shown in FIG. 12F. After biosensor 1222 and needle 1224 are inserted into the user, distal movement of biosensor carriage 1223 is impeded by a chassis or housing containing the needle deployment mechanism. As shown in FIG. 12G, at the point when distal movement of biosensor carriage 1223 is impeded, needle carriage 1225 and biosensor carriage 1223 become disengaged. At this point, a second compression spring 1227 drives the disengaged needle carriage 1225 in a proximal direction, thus withdrawing needle 1224 from the user while biosensor 1222 remains inserted, as shown in FIG. 12H.

Figure 12I:
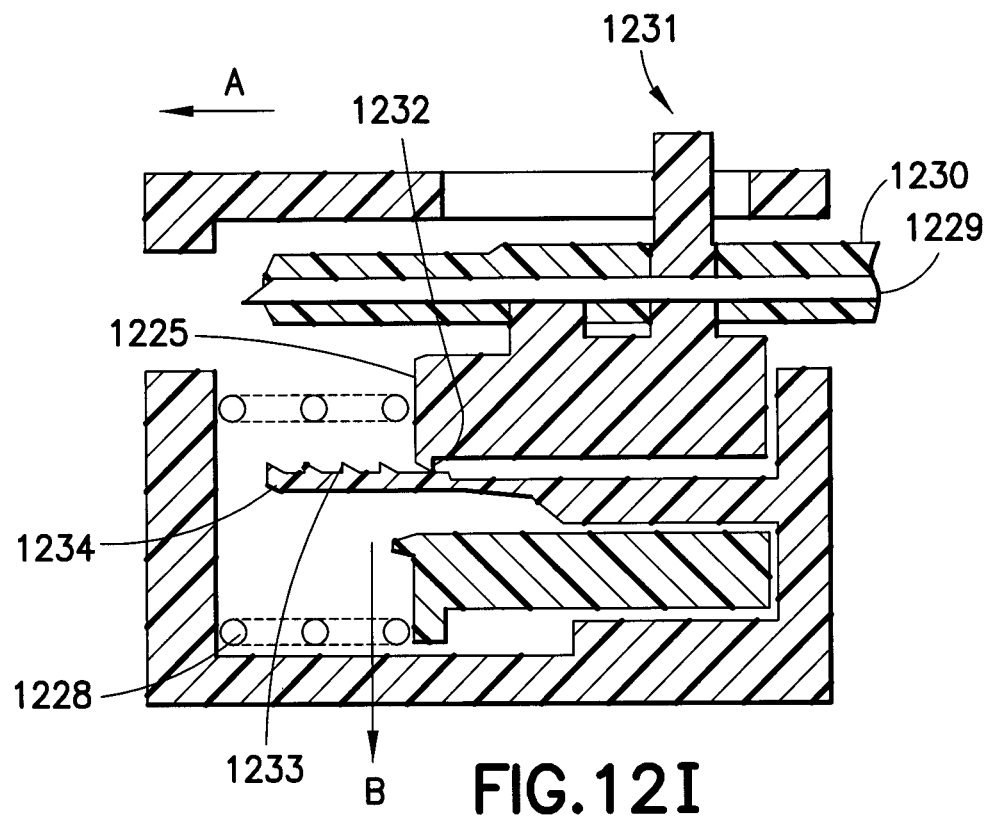
FIGS. 12I-12J illustrate an exemplary embodiment of a manually actuated cannula deployment mechanism with a user controlled carriage for use in an exemplary embodiment of the present invention.
Figure 12J:
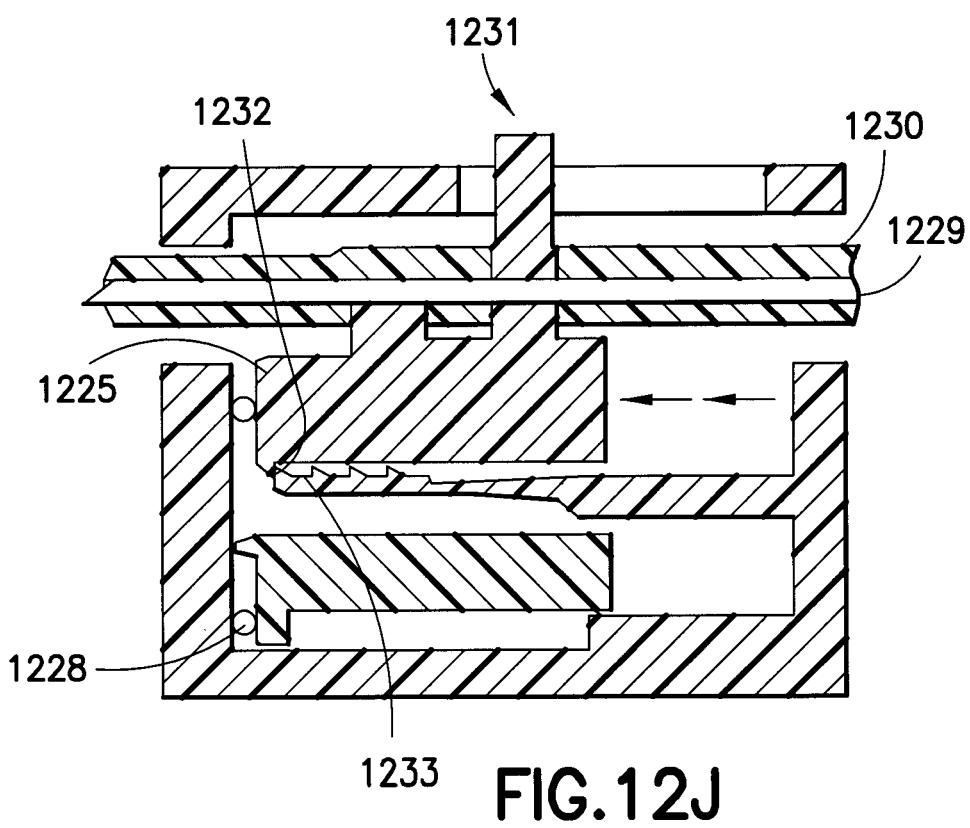

FIGS. 12I-12J illustrate another deployment mechanism for an in-dwelling needle and cannula for use in a medical device according to an embodiment of the present invention. Rather than being triggered as in previously described mechanisms, the needle deployment can be user controlled. That is, carriage 1225 is biased in a retracted position by compression spring 1228. FIG. 12I shows the device in the retracted position, such that needle 1229 and cannula 1230 do not protrude from the chassis. Carriage 1225 includes a manual actuator 1231 which is accessible to the user. When the user moves manual actuator in the direction of arrow 'A' with enough force to overcome the spring bias, the carriage 1225, along with needle 1229 and cannula 1230 move in the direction of arrow 'A'. Carriage 1225 also includes a finger latch 1232 which mates with retention surfaces 1233 on retention latch 1234. As carriage 1232 moves in the direction of arrow 'A' interference between finger latch 1232 and retention surfaces 1233 cause retention latch 1234 to displace in the direction of arrow 'B'. Finger latch 1232 and retention surfaces 1233 are shaped such that as the finger latch moves past each retention surface 1233, carriage 1225 is prevented from moving backwards in the retracted direction. As the carriage moves in the direction of arrow 'A' the needle and cannula protrude from the chassis and enter the user's skin surface. Cantilevered retention latch 1234 can be flexed downward in the direction of arrow 'B' to release the carriage 1225 an retract the needle and cannula. As will be appreciated by those of ordinary skill in the art, any suitable arrangement to release carriage 1225 by flexing retention latch 1234 downward may be employed. Such arrangements may include manual movement by the user via a device provided on the exterior of the chassis, or automatic electronic release via an appropriate command on a PDM.

The combinations and arrangements of the above system components, as illustrated in FIGS. 2-5, are not intended to be limiting. One of ordinary skill in the art will appreciate that any of the above components may be combined and arranged as desired in any of the above exemplary embodiments for realizing a specific drug therapy tailored for each user. Additional exemplary embodiments of medical device 100 utilizing a combination of the above described components for realizing a specific drug therapy are illustrated in FIGS. 13-15.

Figure 13:
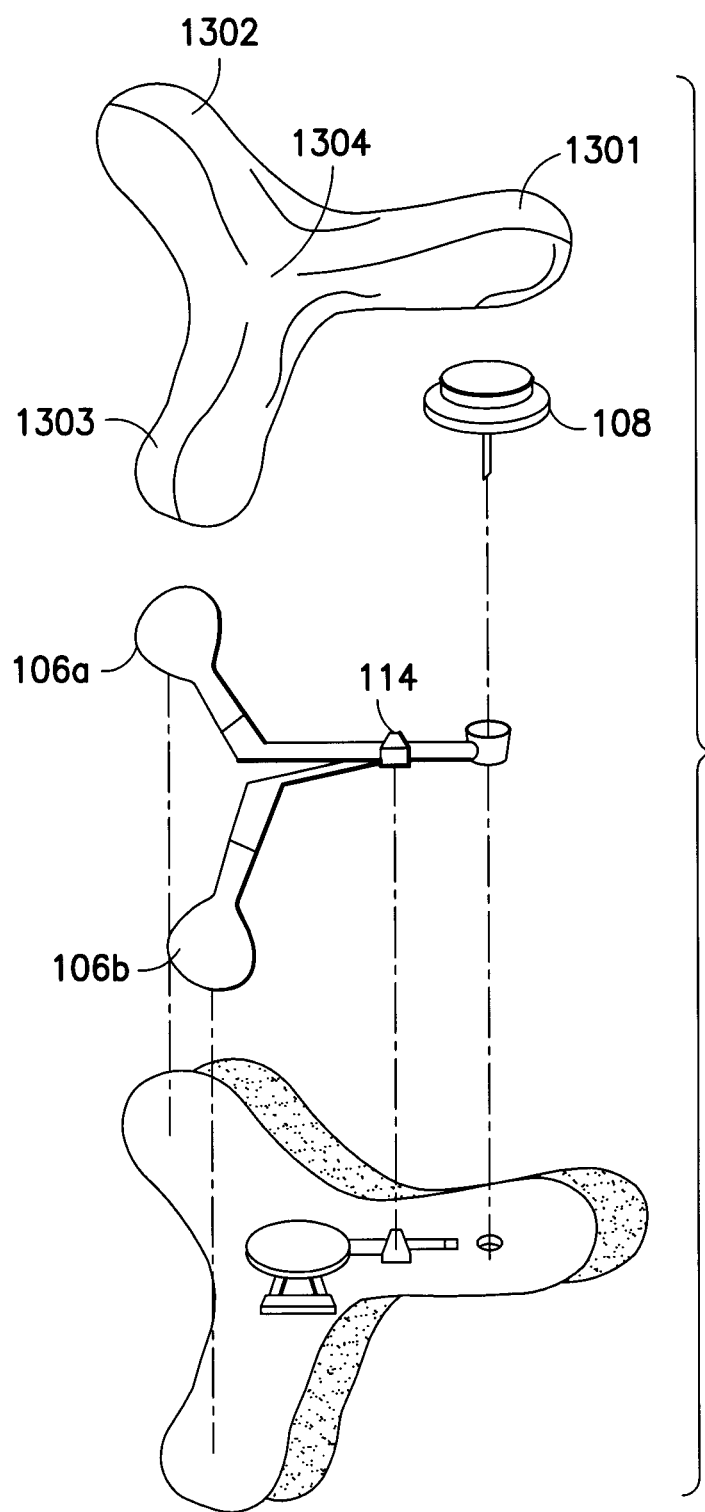
FIGS. 13-15 illustrate additional embodiments of a medical device in accordance with an exemplary embodiment of the present invention.

FIG. 13 illustrates a specific embodiment of a medical device for providing two-drug therapy through a single infusion cannula provided in a single needle deployment mechanism 108. Reservoirs 106a and 106b are provided in fluid communication with the single infusion cannula and are controlled by a single pumping mechanism 114 and an optional valve mechanism for controlling drug flow from each. Based on the number of components in this embodiment, the upper cover of the medical device is appropriately designed to include three lobes 1301, 1302 and 1303, radially extending from the central hub area 1304. Lobe 1301 preferably contains needle deployment mechanism 108 while lobes 1302 and 1303 preferably contain reservoirs 106a and 106b, respectively.

Figure 14:
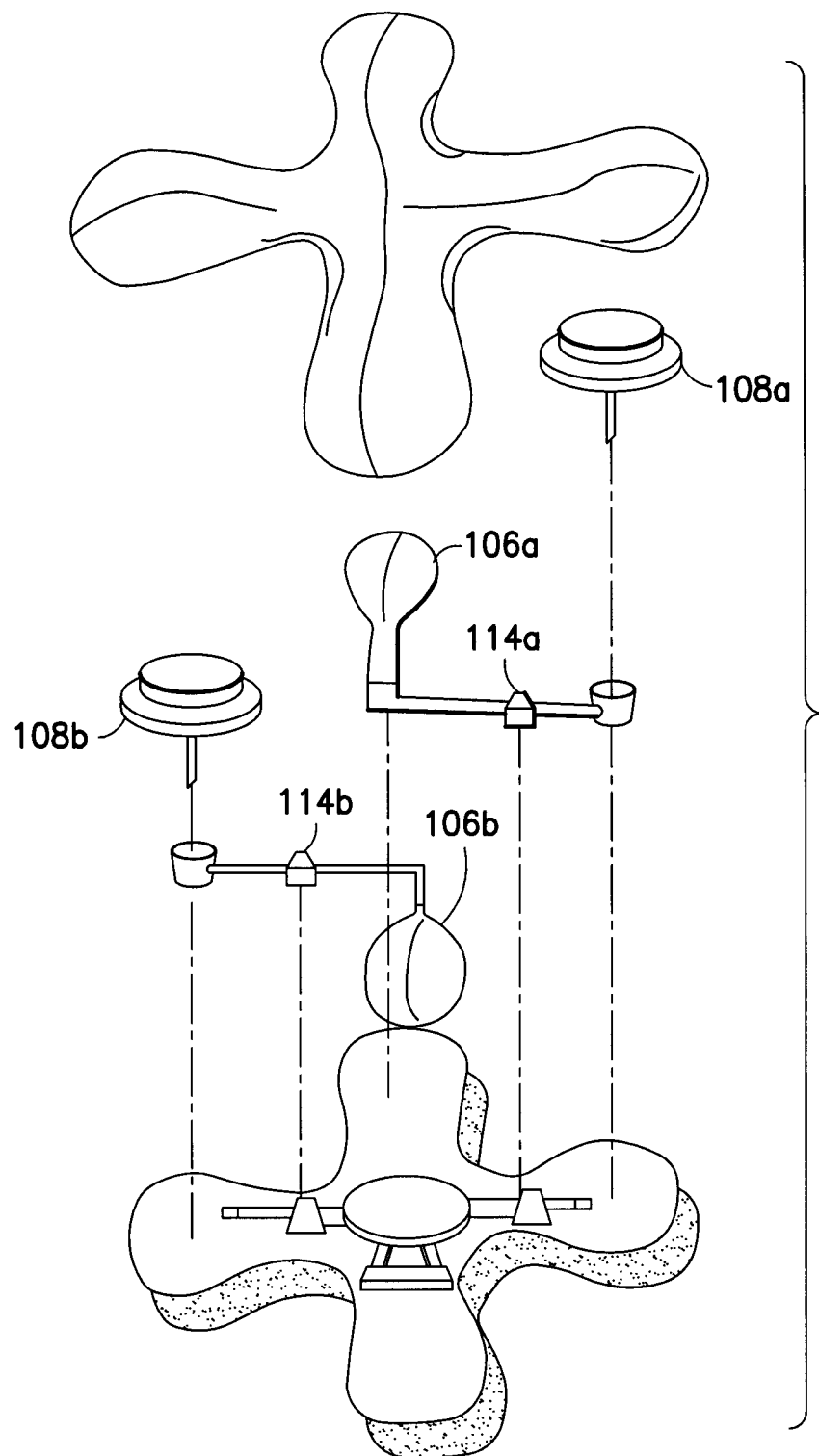

FIG. 14 illustrates another embodiment of a medical device for providing drug therapy through a first and second infusion cannula provided by first and second needle deployment mechanism 108a and 108b. Each infusion cannula is manually or automatically actuated as described above. In one embodiment, the flexible upper cover may provide access to a push button for manually actuating each needle deployment mechanism 108 and 108b. Each infusion cannula may be in fluid connection with its own reservoir 106a or 106b for supplying a two-drug therapy if desired. Alternatively, a single reservoir may be shared by each infusion cannula, thus enabling a back-up or secondary infusion cannula if necessary.

Figure 15:
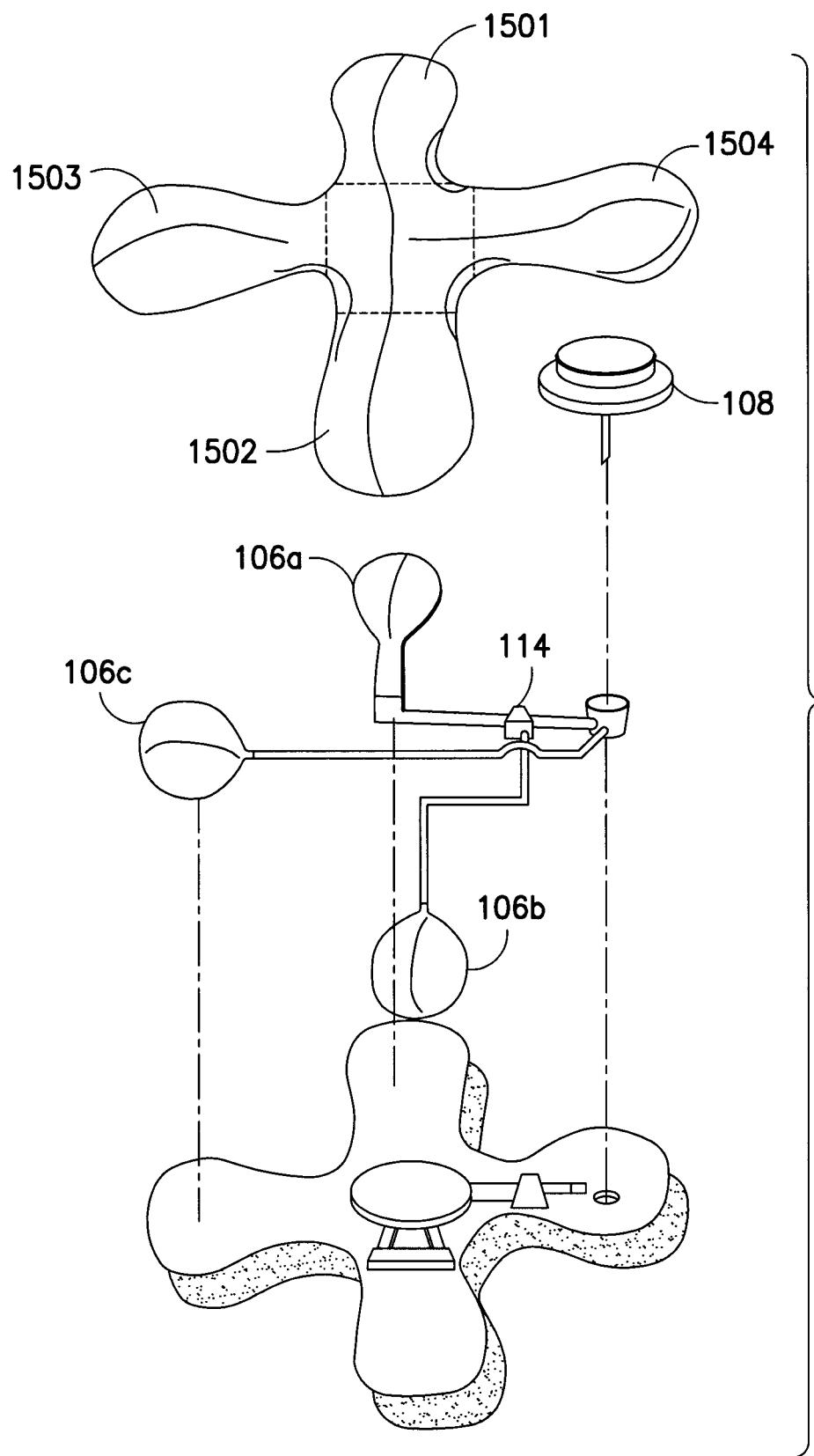

FIG. 15 illustrates another embodiment for providing up to three-drug therapy through a single infusion cannula. First and second reservoirs 106a and 106b are shown as connected to a single pumping mechanism 114 with an optional valve for controlling a drug flow from each. Additionally, a third reservoir 106c may be provided directly to the infusion cannula, as shown, for enabling a manual bolus dose of drug as desired. Because of the thin, flexible nature of the upper cover of the medical device, a user may manually actuate a bolus dose by applying a force to a specific area of the upper cover. The specific area is preferably adjacent to the reservoir 106c for holding a supply of drug to be provided in the bolus dose. The reservoir 106c is preferably located in a particular lobe (1503) of the device so the user can press the lobe 1503 to effect a bolus dose. The force applied by the user may expel a volume of drug from the reservoir to be provided to the user through the infusion cannula. Optionally, the force applied by the user may close an electrical contact that automatically actuates injection of a bolus dose via an electronic pump mechanism and controller, as will be understood by one of ordinary skill in the art. In another embodiment, the medical device may be designed to provide only a bolus dose of one or more drugs contained in one or more reservoirs through one or more infusion cannulas, as similarly provided above.

The additional embodiments shown in FIGS. 13-15 illustrate only a few of the myriad embodiments and arrangements enabled by the present invention, as will be appreciated by one of ordinary skill in the art. The specific combination of components described above, particularly the number of reservoirs and the drugs stored therein, may be chosen for providing specific treatment to a user suitable for the user's medical condition, among other factors. Particularly, an exemplary medical device may initially be provided for treatment of Type II diabetes by administering only multiple daily injections or only bolus doses of a single drug or a number of drugs. As a user's disease state progresses to increasing levels of insulin resistance, a similar medical device with another combination or arrangement of components may be used for more effective treatment.

Additionally, the features of the above exemplary embodiments may be similarly provided in a number of applications and are not limited to the above disclosure. Any other skin-surface, wearable, devices can utilize the above features and techniques for providing utmost comfort and convenience through maximum flexibility and conformity of the wearable device. In addition to the insulin patch pump devices disclosed herein, other drug therapy, such as for the treatment of rheumatoid arthritis, or the infusion of Human Growth Hormone, may ideally be provided through a wearable medical device disclosed above, especially for children or the elderly for whom the thin lightweight medical device 100 is ideal.

Figure 16:
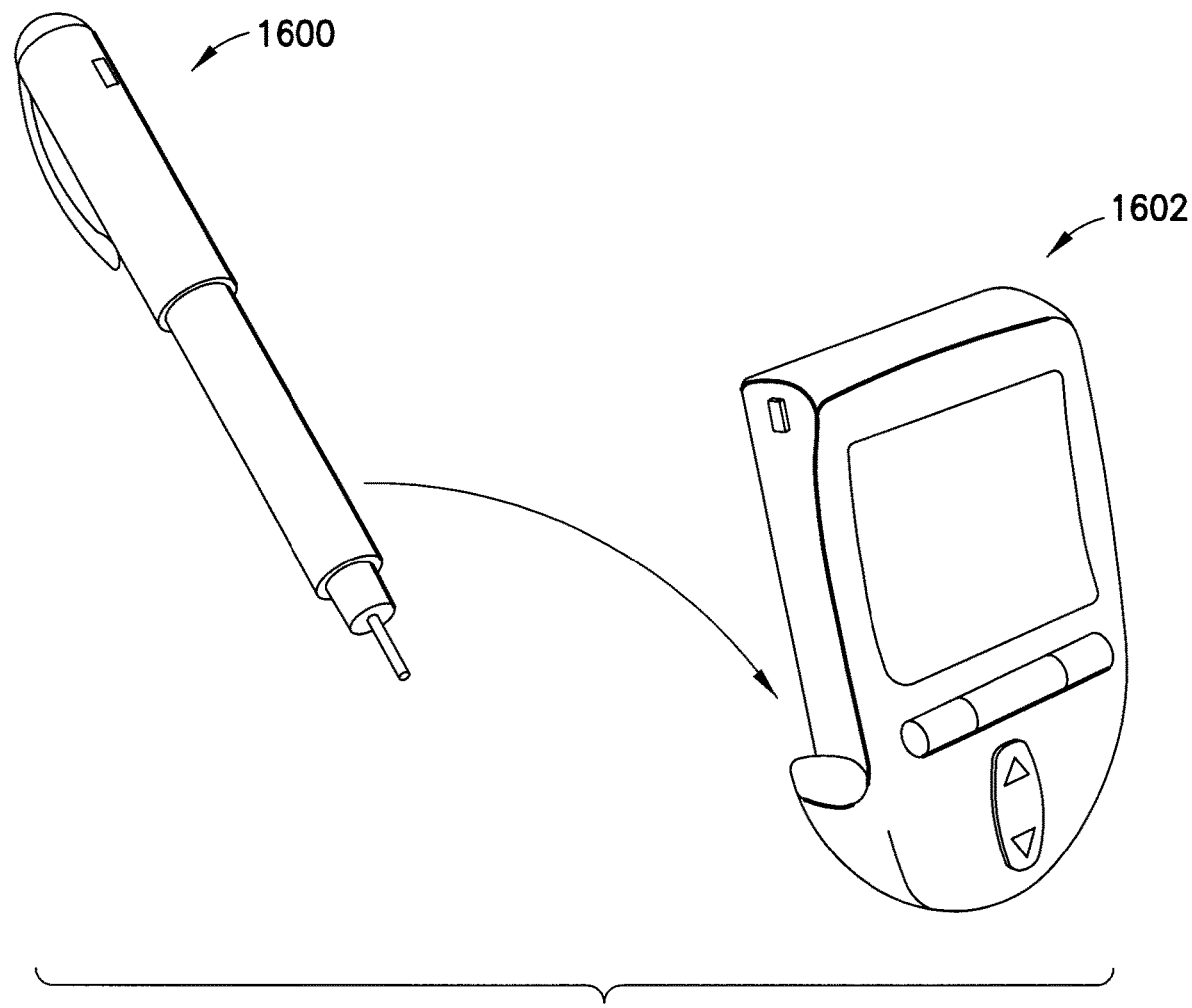
FIG. 16 illustrates an additional embodiment of a drug delivery device in accordance with an exemplary embodiment of the present invention.

A medical device, in any of the exemplary embodiments described above, may also be used in conjunction with a programmable drug delivery device 1600, such as a programmable insulin pen, as shown in FIG. 16. In a preferred embodiment, a wearable medical device is configured to provide only a preset, pre-programmable or programmable basal rate of infusion, whereas programmable drug delivery device 1600 is provided for infusing necessary bolus dosages. While certain embodiments of the wearable medical devices discussed above are capable of providing a bolus dose, some users may be more comfortable with and prefer to use a familiar pen injection device such as that shown in FIG. 16. Additionally, for some users, drug therapy provided by an insulin pen device alone, may be an effective treatment. Common mechanical insulin pen injection devices typically require user interaction to accurately set a desired dosage for the injection. Conventional mechanical pens generally include small dosage graduations that may be difficult to see or accurately set. As such, a programmable insulin pen device 1600, in exemplary embodiments of the present invention would eliminate the potential for dosage errors resulting from a user's inability to properly operate the device.

In one embodiment of the present invention, when not in use, drug delivery device 1600 preferably remains attached to a Personal Diabetes Manager (PDM) 1602, Blood Glucose Monitor (BGM), or other device for calculating a bolus dose. When a user instructs PDM 1602 to calculate a bolus dose requirement, the PDM calculates the dose from either a basal rate infusion history or a user's blood glucose level, and automatically programs the dose into drug delivery device 1600 without any further calculation, setting or adjustment required by the user. PDM 1602 may also comprise a sensing mechanism or other system for determining a blood glucose level, which it uses to calculate a desired bolus dose for the user. This exemplary embodiment of the present invention reduces the number of steps necessary for infusion and reduces dosage errors caused by a user's inability to properly operate common, mechanical insulin pens.

Drug delivery device 1600 in an exemplary embodiment, preferably includes a replaceable insulin cartridge and may be cylindrical in form, similar to insulin pens that are commonly available. The dose mechanization typically located in the upper portion of common insulin pens is preferably replaced by a flex circuit which is wrapped around the inner diameter of the pen barrel. A rechargeable battery may be provided on the centerline of the barrel inside the flexible circuit. The replaceable insulin cartridge would be located in the lower portion of the pen, and a micro-pump is provided between the insulin cartridge and a pen needle. Alternately, a linear actuator can be placed inside the flexible circuit in line with the insulin vial. The linear actuator applies a force to drive the plunger in the vial, resulting in a bolus dose equal to the displaced volume of the plunger movement. Very small linear actuators are available and may advantageously used for this purpose. One example is the Squiggle® linear actuator manufactured by New Scale Technologies. The upper and lower portions of the pen preferably separate in order to replace the insulin cartridge, and when reassembled, provide an electrical connection to the micropump. Each time drug delivery device 1600 is attached to PDM 1602, the rechargeable battery in the delivery device 1600 may be charged, and an infusion history or blood glucose history that is stored in the pen may automatically be uploaded to the PDM 1602.

An exemplary embodiment of the present invention may provide drug delivery device 1600 with the low cost components necessary for communicating via a personal area network as described in previously incorporated, co-pending U.S. application Ser. No. 12/458,807. This embodiment enables continued communication between the drug delivery device 1600 and PDM 1602 or a "smart" wearable medical device as disclosed in the exemplary embodiments above. The "smart" medical device or PDM may automatically program drug delivery device 1600 each time a bolus dose is calculated, as long as both are in physical communication with the user's body. A "smart" wearable medical device containing a biosensor, or otherwise in communication with a biosensor, may also be capable of providing bolus dosage requirements to the drug delivery device 1600 to be automatically programmed by the device based on a user's blood glucose level. Additionally, drug delivery device 1600 may automatically update via the personal area network, the PDM or "smart" medical device each time a bolus dose is administered to the user. The above embodiments provide a low-cost, intelligent device capable of further enhancing the functionality of the exemplary wearable medical devices disclosed above, in an embodiment that is easy to use and familiar to many users requiring insulin therapy.

While the present invention has been shown and described with reference to particular illustrative embodiments, it is not to be restricted by the exemplary embodiments but only by the appended claims and their equivalents. It is to be appreciated that those skilled in the art can change or modify the exemplary embodiments without departing from the scope and spirit of the present invention.

What is claimed is:

1. A wearable medical device for administering drug therapy to a user, said medical device comprising:
    an integral housing comprised of a flexible upper portion and a flexible lower portion joined together along respective perimeters of each portion to form a hollow volume therebetween, the hollow volume enclosing at least one pump component in a watertight manner, wherein said upper and lower portions comprise at least one recess extending inwardly from an outer edge of each of said upper and lower portions that increases flexibility of a bottom surface of the medical device; and
    a thermal bubble micropump sealed between the flexible upper portion and the flexible lower portion.

2. The medical device of claim 1, further comprising a second recess extending inwardly from an outer edge of each of said upper and lower portions at a location opposite the at least one recess.

3. The medical device of claim 2, wherein the first and second recesses define a flex region that separates a first area of the device from a second area of the device.

4. The medical device of claim 3, wherein a first system component is contained within the first area and a second system component is contained within the second area.

5. The medical device of claim 1, wherein the thermal bubble micro pump comprises:
    a fluid flow path having comprising a proximal end and a distal end,
    a first one-way valve arranged at a proximal end of the fluid flow path permitting fluid flow in the distal direction but restricting fluid flow in the proximal direction; and
    a second one-way valve arranged at a proximal end of the fluid flow path permitting fluid flow in the distal direction but restricting fluid flow in the proximal direction.

6. The medical device of claim 5, further comprising a thermal resistor located within the fluid flow path between the first and second one-way valves.

7. The medical device of claim 6, further comprising a plurality of thermal resistors.

8. The medical device of claim 1, wherein the thermal bubble micro pump comprises:
    three thermal resistors located within the fluid flow path, and an electronic gate for controlling flow of fluid through the fluid flow path.

9. The medical device of claim 1, further comprising a micropump, the micropump comprising:
    a fluid flow path having comprising a proximal end and a distal end,
    a first one-way valve arranged at a proximal end of the fluid flow path permitting fluid flow in the distal direction but restricting fluid flow in the proximal direction;
    a second one-way valve arranged at a proximal end of the fluid flow path permitting fluid flow in the distal direction but restricting fluid flow in the proximal direction; and
    a variable volume holding chamber between the first and second one-way valves and controllable to change volume and thereby cause fluid to flow in the fluid flow path.

10. The medical device of claim 1, further comprising a micropump, the micropump comprising:
    a fluid flow path having comprising a proximal end and a distal end,
    a first one-way valve arranged at a proximal end of the fluid flow path permitting fluid flow in the distal direction but restricting fluid flow in the proximal direction;
    a second one-way valve arranged at a proximal end of the fluid flow path permitting fluid flow in the distal direction but restricting fluid flow in the proximal direction; and
    a bellows fluid chamber between the first and second one-way valves and controllable to change volume and thereby cause fluid to flow in the fluid flow path.

11. The medical device of claim 10, further comprising a thermal resistor and thermal expansion membrane adapted to controllably change the volume of the bellows fluid chamber.

12. The medical device of claim 1, further comprising a micropump, the micropump comprising:
    a fluid flow path having comprising a proximal end and a distal end,
    a Belleville spring pressurizing fluid within the fluid flow path, and
    an electronic gate controllably opening or closing the fluid flow path distally from said Belleville spring.

13. The medical device of claim 1, further comprising a micropump, the micropump comprising:
    a fluid flow path having comprising a proximal end and a distal end,
    a MEMS diaphragm nanopump provided in the fluid flow path.

14. The medical device of claim 6, wherein the thermal resistor further comprises a thermal expansion membrane that expands in volume in responses to heating a cavity within the thermal expansion membrane by the thermal resistor.

* * * * *